US007090829B2

(12) United States Patent
Yalpani

(10) Patent No.: US 7,090,829 B2
(45) Date of Patent: Aug. 15, 2006

(54) IMAGING PROBES

(75) Inventor: Manssur Yalpani, Rancho Sante Fe, CA (US)

(73) Assignee: CarboMer, Inc., San Diego, CA (US)

( * ) Notice: Subject to any disclaimer, the term of this patent is extended or adjusted under 35 U.S.C. 154(b) by 280 days.

(21) Appl. No.: 10/411,977

(22) Filed: Apr. 11, 2003

(65) Prior Publication Data

US 2003/0198599 A1    Oct. 23, 2003

Related U.S. Application Data

(60) Provisional application No. 60/372,501, filed on Apr. 11, 2002.

(51) Int. Cl.
*A61B 5/055* (2006.01)
(52) U.S. Cl. ............. 424/9.3; 424/1.11; 424/1.65; 424/9.1
(58) Field of Classification Search ............... 424/1.11, 424/1.65, 9.1, 9.3, 9.4, 9.5, 9.6, 9.7, 1.37, 424/1.8, 1.81, 9.36, 9.37
See application file for complete search history.

(56) References Cited

U.S. PATENT DOCUMENTS

| | | | |
|---|---|---|---|
| 4,366,169 A | 12/1982 | White | |
| 5,342,823 A | 8/1994 | Kuhlmeyer et al. | |
| 5,510,496 A | 4/1996 | Talley et al. | |
| 5,798,406 A | 8/1998 | Feret et al. | |
| 6,011,048 A | 1/2000 | Mathvink et al. | |
| 6,019,959 A | 2/2000 | Platzek et al. | |
| 6,090,793 A | 7/2000 | Zimmermann et al. | |
| 6,218,464 B1 | 4/2001 | Parker et al. | |

FOREIGN PATENT DOCUMENTS

| | | |
|---|---|---|
| WO | WO 93/10440 A1 | 5/1993 |
| WO | WO 99/18133 A1 | 4/1999 |
| WO | WO 00/40252 | 7/2000 |

OTHER PUBLICATIONS

Zakian, K. et al., "Developments in Nuclear Magnetic Resonance Imaging and Spectroscopy: Application to Radiation Oncology", *Seminars in Radiation Oncology*, Jan. 2001, pp. 3-15, vol. 11, No. 1, W.B. Saunders Company.
Duarte, M. et al., "Synthesis Characterization, and Relaxivity of Two Linear Gd(DTPA)—Polymer Conjugates", *Bioconjugate Chem.*, 2001, pp. 170-177, vol. 12, No. 2, American Chemical Society.
Lanza, R. et al., "Transplantation of islets using microencapsulation: studies in diabetic rodents and dogs", *J. Mol. Med.*, 1999, pp. 206-210, vol. 77, Springer-Verlag.
Liu, E. et al., "Transplantation of the Islets of Langerhans: New Hope for Treatment of Type 1 Diabetes Mellitus", *Trends Endocrinol. Metab.*, 2000, vol. 11, No. 9, Elsevier Science B.V.
Nöth, U. et al., "F-MRI In Vivo Determination of the Partial Oxygen Pressure in Perfluorocarbon-Loaded Alginate Capsules Implanted Into the Peritoneal Cavity and Different Tissues", *Magnetic Resonance in Medicine*, 1999, pp. 1039-1047, vol. 42, Wiley-Liss, Inc.
Riess, J., "Blood substitutes and other potential biomedical applications of fluorinated colloids", *Journal of Fluorine Chemistry*, 2002, pp. 119-126, vol. 114, Elsevier Science B.V.
Riess, J., "Fluorocarbon-Based in vivo Oxygen Transport and Delivery Systems", *Vox. Sang.*, 1991, pp. 225-239, vol. 61, S. Karger AG, Basel.
Riess, J. et al., "Design, Synthesis and Evaluation of Fluorocarbons and Surfactants for In Vivo Applications New Perfluoroalkylated Polyhydroxylated Surfactants", *Biomat., Art, Cells, Art, Org.*, 1988, pp. 421-430, vol. 16, Nos. 1-3.
Shapiro, A. et al., "Islet Transplantation in Seven Patients with Type 1 Diabetes Mellitus using a Glucocorticoid-Free Immunosuppressive Regimen", *The New England Journal of Medicine*, Jul. 27, 2000, pp. 230-238, vol. 343, No. 4, Massachusetts Medical Society.
Soon-Shiong, P. et al., "Insulin Independence In a type 1 diabetic patient after encapsulated islet transplantation", *The Lancet*, Apr. 16, 1994, pp.. 950-951, vol. 343.
Sotak, C. et al., "A New Perfluorocarbon for Use in Fluorine-19 Magnetic Resonance Imaging and Spectroscopy", *Magnetic Resonance in Medicine*, 1993, pp. 188-195, vol. 29, Williams & Wilkins.
Tait, J. et al., "Phospholipid Binding Properties of Human Placental Anticoagulant Protein-1, a Member of the Lipocortin Family", *The Journal of Biological Chemistry*, May 15, 1989, pp. 7944-7949, vol. 264, No. 14, The American Society for Biochemistry and Molecular Biology, Inc.
Tait, J. et al., "Development and Characterization of Annexin V Mutants with Endogenous Chelation Sites for $^{99m}$Tc", *Bioconjugate Chem.*, 2000, pp. 918-925, vol. 11, American Chemical Society.
Tanaka, K. et al., "Preparation and Characterization of a Disulfide-Linked Bioconjugate of Annexin V with the B-Chain of Urokinase: An Improved Fibrinolytic Agent Targeted to Phospholipid-Containing Thrombi", *Biochemistry*, 1996, pp. 922-929. vol. 35, American Chemical Society.
Zhao, M. et al., "Non-invasive detection of apoptosis using magnetic resonance imaging and a targeted contrast agent", *Nature Medicine*, Nov. 2001, pp. 1241-1244, vol. 7, No. 11, Nature Publishing Group.

*Primary Examiner*—Dameron L. Jones
(74) *Attorney, Agent, or Firm*—Saliwanchik, Lloyd & Saliwanchik

(57) ABSTRACT

The present invention relates to fluorinated and paramagnetic polyuronides (Formulas I–IV) and proteins useful as imaging probes, diagnostic agents and contrast agents. Additionally, the present invention relates to imaging methods employing the present compounds of Formulas I–IV.

8 Claims, 6 Drawing Sheets

IMAGING PROBES

CROSS-REFERENCE TO A RELATED APPLICATION

This application claims the benefit of provisional patent application Ser. No. 60/372,501, filed Apr. 11, 2002, which is hereby incorporated by reference in its entirety.

FIELD OF THE INVENTION

The present invention relates to novel imaging probes and methods for using the probes in diagnostic imaging processes and other imaging processes to determine physiological functions. Additionally, the present invention relates to implants encapsulated with the present imaging probes.

BACKGROUND OF THE INVENTION

Diabetes is a devastating disease of immense proportions. It is characterized by an impaired glucose metabolism that leads to, among other things an elevated blood glucose level (hyperglycemia) in diabetic patients. Type 1 diabetes is caused by autoimmune destruction of insulin-secreting β-cells within islets of Langerhans in the pancreas. Diabetes is classified into type 1, or insulin dependent diabetes mellitus (IDDM), which arises when a patient's β-cells cease producing insulin in their pancreatic glands, and type 2, or non-insulin dependent diabetes mellitus (NIDDM), which occurs in patients with an impaired insulin metabolism and β-cell malfunction. NIDDM usually takes decades to develop and is characterized sequentially by hyperinsulinemia, elevated triglycerides, high blood glucose and finally in late stages β cell fatigue, where insulin levels drop precipitously usually requiring insulin administration to the patient. In IDDM patients, the β-cells are selectively destroyed by an autoimmune process that involves lymphocyte infiltration. Early in the course of NIDDM, β-cell mass increases to meet the demand for more insulin. Loss of β-cell mass may then occur as NIDDM advances. β-Cells secrete insulin in response to changes in blood glucose concentration in highly regulated fashion and are responsible for achieving minute-to-minute regulation within physiological levels. Insulin deficiency results in prolonged hyperglycemia with serious long-term complications. Current treatments (e.g. insulin injections) do not provide tight regulation of blood glucose levels and thus do not alleviate the long-term complications of diabetes. Both naked and encapsulated islet transplantation are being explored as alternative treatments that can provide more physiological blood glucose level control. Islet transplantation is a promising method for restoring normoglycemia and alleviating the long-term complications of diabetes. Widespread application of islet transplantation is hindered by the limited supply of human islets and will require a large increase in the availability of suitable insulin secreting tissue as well as robust quality assessment methodologies that will ensure safety and in vivo efficacy.

The transplantation of immunoprotected insulin-secreting, glucose-responsive cells is a promising method for the long-term treatment of type 1 diabetes. A limitation that needs to be addressed before this methodology is implemented at a large-scale is cell availability. Human islets cannot be amplified in culture while retaining their differentiated secretory properties, so tissue from at least one human donor is needed for a single treatment of one recipient. The tissue availability limitation can be addressed by employing xenogeneic tissue (such as porcine islets) that is protected from the host's immune response. Immunoprotection can be achieved by enclosing the cells in a permselective membrane allowing passage of low molecular weight nutrients and metabolites, including insulin, but excluding larger antibodies and cytotoxic cells of the host. Most of the experimental work on encapsulated cell therapies has employed alginate as the encapsulating matrix. This methodology is particularly promising because it has the potential of restoring physiological regulation of blood glucose levels without the need for life long immunosupressive therapy. The feasibility of this approach in restoring normoglycemia has been demonstrated for diabetic animals and human with promising results (P. Soon-Shiong, et al., *Lancet*, 343, 950–1, 1994; R. P. Lanza, D. M. Kuhtreiber, et al., *Transplant. Res.*, 28, 820, 1996; E. H. Liu, K. C. Herold, *Trends Endocrinol. Metab.* 11, 379–82, 2000; A. M. Shapiro, J. R. Lakey, et al., *N. Engl. J. Med.*, 343, 230–238, 2000.).

Individuals at risk for developing IDDM can be identified by certain techniques. Those at risk for NIDDM are identifiable through family history and measurement of insulin resistance. However, little is known about the natural history of β-cell mass, turnover and cell lifetime, or the course of inflammation in diabetes. This is attributable to the highly heterogeneous nature of the pancreas, difficulties in its biopsy, and the low volume of β-cell mass (only 1–2% of the organ). Although insulin secretory capacity can be measured, it poorly reflects β-cell mass. There is therefore a substantial need for diagnostic methods that would enable (i) high-risk individuals to be monitored prior to onset of diabetes; (ii) diabetes patients to be monitored over the course of their disease to determine the exact stage of their disease; and (iii) also monitoring responses to therapy.

Current therapeutics for Type 1 diabetics are insulin or insulin mimetics, while most type 2 diabetic patients are treated either with agents that stimulate β-cell function or enhance the patient's tissue sensitivity towards insulin. Several classes of drugs are available for diabetes therapy. These include: insulin, or insulin mimetics; insulin sensitizers including (a) biguanides such as Metformin (b) retinoid-X-receptor (RXR) and peroxisome proliferator activated receptor (PPAR) agonists, such as the Thiazolidinedione (glitazone)and PPAR-γ agonists, e.g., Rosiglitazone and Troglitazone; (c) sulfonylureas (SU), such as Gliclazide, Glimepiride, Glipizide, Glyburide, Tolbutamide and Tolcyclamide; (d) amino acid and benzoic acid derivatives, such as Nateglinide and Repaglinide; (e) α-glucosidase inhibitors, such as Acarbose; (f) cholesterol lowering agents, such as (i) HMG-CoA reductase inhibitors, e.g., Lovastatin, and other statins), (ii) bile acid sequestrants, e.g., Cholestyramine (iii) nicotinic acid (iv) proliferator-activator receptor α-agonists, such as Benzafibrate, and Gemfibrozil, (v) cholesterol absorption inhibitors, e.g., β-sitosterol and (vi) acyl CoenzymeA:cholesterol acyltransferase inhibitors, e.g., Melinamide, and (g) Probucol.

Whilst continuous efforts are directed at developing new anti-diabetic agents, there is also a considerable need for the development of materials related to known therapeutic agents that may display improved bioavailability, functionality or reduced levels of undesirable effects. There is also a need for new diagnostic agents that can facilitate elucidation of the mechanism of insulin release or sensitization and the binding mechanism of the known anti-diabetic agents to their respective molecular receptors.

Fluorocarbon compounds and their formulations have numerous applications in medicine as therapeutic and diagnostic agents and as blood substitutes. Fluorine features a van der Waals radius (1.2A) similar to hydrogen (1.35A). Hydrogen replacement (with F) does therefore not cause significant conformational changes and fluorination can lead to increased lipophilicity, enhancing the bioavailability of many drugs. Fluorinated materials are often biologically inert and are generally expected to reduce side-effect profiles of drugs. The carbon-fluorine bond strength (460 kJ/mol in $CH_3F$) exceeds that of equivalent C—H bonds. Perfluorocarbons (PFCs) display high chemical and biological inertness and a capacity to dissolve considerable amounts of gases, particularly oxygen, carbon dioxide and air per unit volume. PFCs can dissolve about a 50% volume of oxygen at 37° C. under a pure oxygen atmosphere. Fluorocarbon compositions can be used for wound treatment, as described in U.S. Pat. No. 4,366,169. Fluorocarbon formulations are also useful in diagnostic procedures, for example as contrast agents (Riess, J. G., *Hemocompatible Materials and Devices: Prospectives Towards the 21st Century*, Technomics Publ. Co, Lancaster, Pa. USA, Chap 14 (1991); *Vox Sanguinis*, 61:225–239, 1991).

Nuclear magnetic resonance (NMR) techniques permit the assessment of biochemical, functional, and physiological information from patients. Magnetic resonance imaging (MRI) of tissue water can be used to measure perfusion and diffusion with submillimeter resolution. Magnetic resonance spectroscopy may be applied to the assessment of tissue metabolites that contain protons, phosphorus, fluorine, or other nuclei. The combination of imaging and spectroscopy technologies has lead to spectroscopic imaging techniques that are capable of mapping proton metabolites at resolutions as small as 0.25 $cm^3$ (Zakian K L; Koutcher J A; Ballon D; Hricak H; Ling C C, *Semin Radiat Oncol.*; 11(1):3–15, 2001). In magnetic resonance angiography (MRA) contrast agents are used to image the arteries and veins for diagnosing cardiovascular disease and associated disorders.

Of particular interest is fluorine's diagnostic value in non-invasive imaging applications. Apolar oxygen imparts paramagnetic relaxation effects on $^{19}F$ nuclei associated with spin-lattice relaxation rates ($R_1$) and chemical shifts. This effect is proportional to the partial pressure of $O_2$ ($pO_2$). $^{19}F$ NMR can therefore probe the oxygen environment of specific fluorinated species in cells and other biological structures.

Nöth et al. (Nöth U; Grohn P; Jork A; Zimmermann U; Haase A; Lutz, J., $^{19}F$-MRI in vivo determination of the partial oxygen pressure in perfluorocarbon-loaded alginate capsules implanted into the peritoneal cavity and different tissues, *Magn. Reson. Med.* 42(6):1039–47, 1999) employed perfluorocarbon-loaded alginate capsules in MRI experiments to assess the viability and metabolic activity of the encapsulated materials. Quantitative $^{19}F$-MRI was performed on perfluorocarbon-loaded alginate capsules implanted into rats, in order to determine in vivo the $pO_2$ inside the capsules at these implantation sites. Fraker et al. reported recently a related method with perfluorotributylamine (C. Fraker, L. Invaeradi, M. Mares-Guia, C. Ricordi, PCT WO 00/40252, 2000).

Ideally, PFC imaging agents should combine the following features: non-toxic, biocompatible, chemically pure and stable, low vapor pressure, high fluorine content, reasonable cost and commercial availability. Additionally, they should meet several $^{19}F$-NMR criteria, including a maximum number of chemically equivalent fluorines resonating at one or only few frequencies, preferably from trifluoromethyl functions. Some of the other spectral criteria have been discussed in detail elsewhere (C. H. Sotak, P. S. Hees, H. N. Huang, M. H. Hung, C. G. Krespan, S. Raynolds, *Magn. Reson. Med.*, 29, 188–195, 1993.). For MRI, it would furthermore be desirable to have control over the amount of magnetically responsive material for specific uses, and to employ temperature-responsive and pH-dependent imaging agents for special uses. These could have applications in MRI-based temperature monitoring for use in general hyperthermia treatment (see, e.g., S. L. Fossheim; K. A. ll'yasov, J. Hennig, A. Bjornerud, *Acad. Radiol.*, 7(12),1107–15, 2000.) of tumors and for monitoring the efficacy of chemotherapy, respectively (see, e.g., N. Rhagunand, R. Martinez-Zagulan, S. H. Wright, R. J. Gilles, *Biochem. Pharmacol.*, 57, 1047–1058, 1999; I. F Tannock, D. Rotin, *Cancer Res.*, 49, 4373–4383, 1989.). Furthermore, water solubility would enhance the PFC functionality in many biomedical settings, as it would obviate the need for emulsifiers.

Although selected efforts have been directed at developing new fluorinated MRI probes, none are water soluble compounds [e.g., perfluoro-[15]-crown-5 ether)], and some are commercially unavailable [e.g., perfluoro-2,2,2',2'-tetramethyl-4,4'-bis(1,3-dioxalane)]. It appears no attempts have so far focused on screening available PFCs from the thousands of commercial fluorinated products in order to identify potentially more suitable MRI probes for biomedical uses. It seems furthermore that no studies have attempted to establish structure activity relations (SARs) of related PFCs for MRI purposes. Noteworthy is also the fact that all PFCs examined to date have molecular weights under 1,000, typically between 400–600 Da. This is partly a reflection of the specific requirements for blood substitution agents, but also due to the widely held belief that higher molecular weight or polymeric fluorinated agents would not be detectable by $^{19}F$-NMR due to anticipated excessive line broadening, and would therefore be unsuitable. Thus, with the exception of the polymer-encapsulated PFCs noted above, this important class of materials had so far been excluded from consideration.

Paramagnetic ions, such as gadolinium ($Gd^{3+}$) decrease the $T_1$ of water protons in their vicinity, thereby providing enhanced contrast. Gadolinium's long electron relaxation time and high magnetic moment make it a highly efficient $T_1$ perturbant. Since uncomplexed gadolinium is very toxic, gadolinium chelate probes, such as gadolinium diethylenetriamine pentaacetic acid (GdDTPA $M_w$ 570 Da), albumin-GdDTPA (Gadomer-17, $M_w$ 35 or 65 kDa), have been employed extensively in MRI of tumors and other diseased organs and tissues. Several other developmental chelators have also been reported, including dual-labeled agents, oligonucleotide-derived, dextran-derived GdDTPA, and TAT and other peptide-derived chelators. However, presently approved MRI contrast agents are either not tissue specific, e.g., GdDTPA, or target only normal tissue, which limits their utility in diagnosis of metastases or neoplasia. MRI studies with GdDTPA, for instance, do not correlate with the angiogenic factor or the vascular endothelial growth factor (VEGF). Attempts have also been made to overcome the low relaxivities of small Gd-DTPA chelates by preparing polymer conjugates of $Gd(DTPA)^{(2-)}$ [see e.g., MRA. Duarte M. G.; Gil M. H.; Peters J. A.; Colet J. M.; Elst L. Vander; Muller R. N.; Geraldes C. F. G. C., *Bioconjug. Chem.*, 21, 170–177, 2001.]. However, the relaxivity of these polymer conjugates was only slightly improved and they were also cleared very quickly from the blood of rats, indicating that they are of limited value as blood pool contrast agents for MRI.

Annexin V is a human protein (Mw 36,000) with high affinity for cells or platelet membranes that, following apoptosis (programmed cell death), have redistributed phosphatidylserine (PS) functions from internal to external membrane surfaces (see e.g., Verhoven et al. [B. Verhoven, R. A. Schlege, P. Willamson, *J. Exp. Med.*, 182, 1597–1601, 1995] and Tait et al. [J. F. Tait, D. Gibson, *J. Lab. Clin. Med.*, 123, 741–748, 1994.]). Apoptosis is an integral part of the aging and development of the central nervous system (CNS) and is linked to the pathogenesis of autoimmune and neurodegenerative diseases, cerebral and micordial ischemia, vasogenic edema, viral infections, inflammatory demyelinating diseases, organ and bone marrow transplant rejection, tumor response to chemotherapy and radiotherapy, and trauma [see e.g., H. Steller, Science, 267, 1445–1449, 1995; S. M. de la Monte, Y. K. Sohn, N. Ganju, J. R. Wands, *Lab Invest.*, 158, 1001–1009, 1998.]. Among the neurodegenerative diseases linked to apoptotic events are Alzheimer's disease, Pick's disease, Parkinson's Disease, progressive supranuclear palsy, amyotrophic lateral sclerosis, and diffuse Lewy Body disease. These diseases are believed to share common neurodegenerative mechanisms, but maintain distinct clinical and pathological profiles due to atrophy and cell loss in specific regions of the CNS.

In view of the ubiquitous role of apoptosis in a broad range of disorders, a probe that could identify and quantify cell death in vivo would be of substantial benefit. The study of CNS neuron apoptosis could be a valuable tool for screening more effective drugs in the treatment of dementia associated with Alzheimer's and other diseases. One of the past hurdles in the development of potential therapies has been the general lack of relevant in vitro and in vivo diagnostic methodologies to assess the potential of new therapeutic compounds. Annexin's affinity for PS has been exploited to study in animals and humans hepatic apoptosis, chemotherapy, allograft rejection, and thrombosis, using radioisotope-labeled annexin [see e.g., Blankenberg et al., *Proc. Natl. Acad. Sci. USA*, 95, 6349–6354, 1998; Ohtsuki K; Akashi K; Aoka Y; Blankenberg F. G.; Kopiwoda S; Tait J. F.; Strauss H. W. Eur. J. Nucl. Med., 26, 1251–8, 1999. Blankenberg F. G.; Katsikis P. D.; Tait J. F.; Davis R. E.; Naumovski L.; Ohtsuki K.; Kopiwoda S.; Abrams M. J.; Strauss H. W., *J. Nucl. Med.*, 40, 184–91, 1999. J. R. Stratton, et al., *Circulation*, 92, 3113–3121, 1995.]. Another PS binding protein, the $C_2$ domain of synaptotagmin I, was conjugated to superparamagnetic iron oxide (SPIO) nanoparticles and used in MRI to detect apoptotic cells. Zhou, et al, *Nature Medicine*, Vol. 7, No.: 11, November 2001.

Whilst much can be achieved with currently available imaging and contrast agents, there are still unmet needs for novel diagnostic agents, particularly for those exploiting biological specificity. Imaging agents suitable for targeting metastases or neoplasia would substantially enhance the MRI sensitivity and utility for tumor detection and prevention. Similarly, imaging agents suitable for targeting receptors involved in insulin production and utilization would substantially enhance our understanding of the diabetes disease process and the function of anti-diabetic drugs. Although selected efforts have been directed at developing such new probes, a broader investigation of these agents is urgently needed. Similarly, new imaging probes are needed as noninvasive means to detect and image cells, tissues and organs undergoing apoptosis.

BRIEF SUMMARY OF THE INVENTION

Figure 1A:
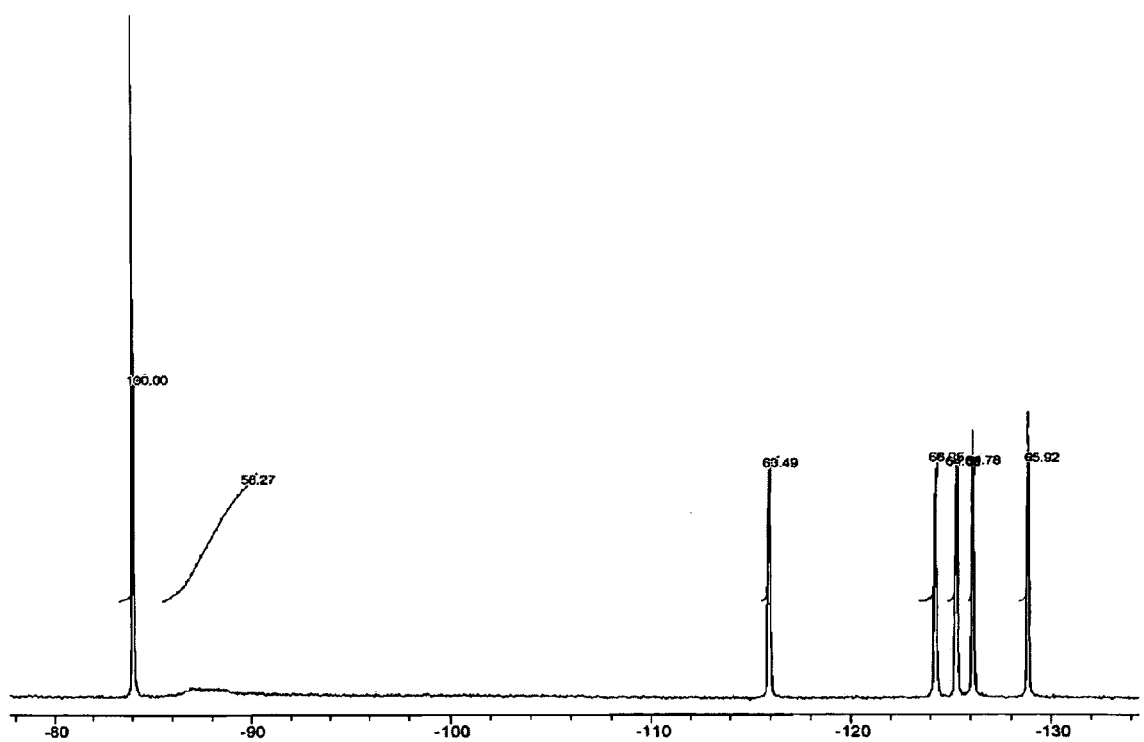
FIGS. 1A–C shows spectra of heptafluorobutyryl alginate of Example 1 in $D_2O$ (a); its expanded trifluoromethyl resonance (b); and (c) $Ca^{2+}$ beads of heptafluorobutyryl alginate in $D_2O$ (376 MHz $^{19}$F-NMR (0.4%)).
Figure 1B:
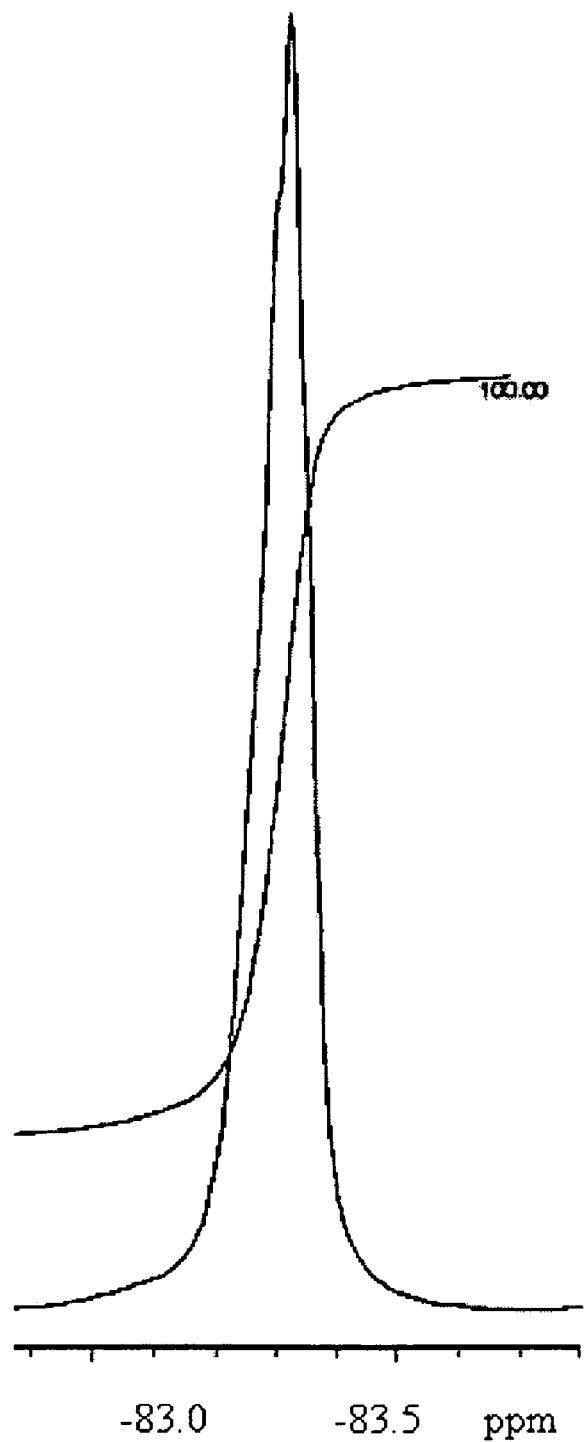

The present invention relates to fluorinated and/or paramagnetic polyuronides (Formulas I–IV) and fluorinated and/or paramagnetic proteins useful as imaging probes, diagnostic agents and contrast agents. Additionally, the present invention relates to imaging methods employing the present compounds of Formulas I–IV and the fluorinated/paramagnetic proteins described herein.

The fluorinated and chemically modified polyuronides of the present invention include compounds of general formulas I to IV below:

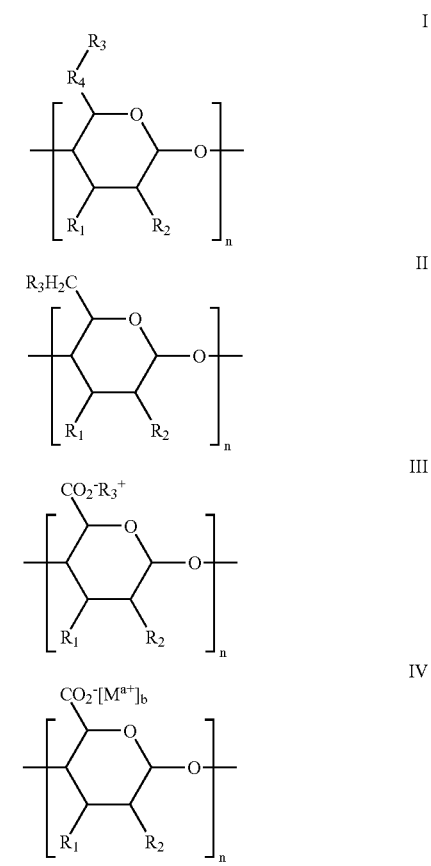

Where

For Formula I:
$R_1$=OH, OX, X; $R_2$=OH, OX, X, NHCOX; $R_3$=OH, OY, OX, NHX, alkyl, alkoxyalkyl; $R_4$ represents C=O, $CH_2$, CNX, $CF_2$; preferably $R_1$ is OH or OX, $R_2$ is OH or OX wherein it is especially preferred that one of $R_1$ and $R_2$ is OH while the other is OX For Formula II:
$R_1$=OH, OX, X, $OR_4$; $R_2$=OH, OX, X, $OR_4$; $R_3$=OH, Y, X, $R_4$; $R_4$=acyl, alkyl or aryl; preferably $R_1$ is OH or OX, $R_2$ is OH or OX, $R_3$ is OH, $R_4$ is C=O, wherein it is especially preferred that one of $R_1$ and $R_2$ is OH while the other is OX For Formula III:

$R_1$=OH, OX, X; $R_2$=OH, OX, X; $R_3$=H, N(X)$_3$ and preferably $R_1$ is OH, $R_2$ is OH and $R_3$ is H or N(X)$_3$ For Formula IV:

$R_1$=OH, OX, X; $R_2$=OH, OX, X, —O—A(X)—O— or —O—A (R$_3$)—O—; R3=alkyl, acyl or M is any paramagnetic ion of the transition metal or lanthanide series, including gadolinium (III), iron (III), manganese (II and III), chromium (III), copper (II), dysprosium (III), terbium (III), holmium (III), erbium (III), and europium (III); most preferred are gadolinium (III), dysprosium (III), iron (III), and manganese (II), and for the ion valency of a=1, b=1; a=2, b=½; a=3, b=⅓; a=4, b=¼; etc.;

A is any non-paramagnetic ion, including fluorinated ammonium salts, e.g., ammonium heptafluorotantatalate (V), ammonium hexafluorogermanate, ammonium hexafluoroniobate, ammonium hexafluorophosphate, ammonium hexafluorostannate, ammonium tetrafluoroborate, antimony(III) or (V) fluoride, barium fluoride, fluoroboron salts, including boron trifluoride and its derivatives, fluorolithiates, including lithium tetrafluoroborate and lithium fluoride, iron (II) fluoride, magnesium fluoride, potassium fluoride, sodium fluoride, and tetralkylammonium fluoride salts, including tetrabutylammonium tetrafluoroborate;

Wherein

X is a fluorine containing moiety. Suitable fluorine moieties include fluoroalkyl, fluoroaryl, fluoroacyl, perfluoroalkyl, perfluoroaryl, perfluoroacyl, perfluoropolymer, fluoroamine, fluorocarbamate, fluorotriazine, fluorosulfonylalkyl derivatives, F, $CF_3$, $COC_xF_y$, $CF_3CO_2$, $C_xF_yH_z$, $([CH_2]_mO)_x(CH_2CF_2O)_y(CF_2CF_2O)_z(CF_2)_2$ $CF_2CH_2O(CH_2)_pOH$, $CH_2C(OH)C_xF_yH_z$, $C_xF_yH_zO_p$, $COC_{x-}F_yH_z$, $OCH_2C_xF_z[C_xF_zO]_mF$, $CH_2C(CH_3)CO_2C_xH_z(CF_2)_m$ $CF_3$, $CH_2(CF_2O)_x(CF_2CF_2O)_y(CF_2O)_zCF_2CH_2OH$, $NHC_{x-}F_yH_zO_p$, $CH_2CF_2O[CF_2CF_2O]_mCF_2OCF_2CH_2OH$, $COC_xH_z$ $(CF_2)_mCF_3$, $CO-CF_2O[CF_2CF_2O]_nCF_2OCF_2CO_2H$, $CO-CF(CF_3)[CF(CF_3)CF_2O]_mF$ $([CH_2]_mO)_x(CH_2CF_2O)_y$ $(CF_2CF_2O)_zCF_2CH_2O(CH_2)_pOH$, $SO_2[CF_2]_xCF_3$, $CF_3SO_3$, $N[C_xF_yH_z]_p$, $C_xH_zCO_2C_xH_z(CF_2)_mCF_3$, $COC_xF_y[C_pF_zO]_mF$, a luminescent residue, a fluorescent residue, a fluorinated luminescent residue or a fluorinated fluorescent residue, Y=$CH_2C(OH)CH_3$, and m, p, x, y, z=0–150 and where m is more preferably 10–100, and most preferably 10–50, and where x, p, y, z are more preferably 10–75, even more preferably 10–50, and most preferably 10–20. and where n is more preferably 10–10,000, even more preferably 10–1,000, and most preferably 10–250. Preferred compounds of Formula IV are those where $R_1$ and $R_2$ are both OH.

Acyl and alkyl residues of Formulas I to IV comprise lipophilic moieties, including saturated and unsaturated aliphatic residues with $C_k$ chains, where k is 2 to 100, more preferably 2–50, and most preferably 2–20, and where aryl residues comprise aromatic moieties, including benzyl, biphenyl, phenyl, polycyclic aromatics, and heteroatom-containing aromatics. The novel fluorinated and paramagnetic polyuronides of Formulas I to IV comprise polyuronide analogs, wherein said polyuronides are selected from the group consisting of acacia, alginate, gellan, glycosaminoglycans, hyaluronate, polymannuronic acid, polyguluronic acid, pectins, propyleneglycol alginate, acacia, carboxyalkyl glycans, including carboxymethyl amylose, carboxymethyl cellulose, carboxymethyl dextran, carboxymethyl starch, starch, hydroxyethyl starch, hetastarch, pentastarch, dextran, tragacanth and xanthan. Pharmaceutically acceptable salts of the above fluorinated polyuronides are also contemplated by the present invention. When more than one designated substituent or moiety (for example X) appears in a formula for a compound, then the substituent can be the same or different at the various positions of that substituent in the formula for that compound.

Disclosed are novel compositions comprising fluorinated and chemically modified proteins with activity or affinity for cells, cell surfaces, membranes, cell surface receptors, and receptors regulating biological membrane channels. The fluorinated and/or paramagnetic proteins are useful as imaging probes and diagnostic agents. Exemplary proteins include fluorinated analogs of Annexin V and synaptotagmin I and superparamagnetic Annexin V iron oxide conjugates and synaptotagmin I iron oxide conjugates.

DETAILED DESCRIPTION OF THE INVENTION

In practicing the present invention a polyuronide or a protein that binds with a receptor is modified with a fluorine containing moiety and/or a paramagnetic ion to produce an analog that is useful in MRI imaging processes as imaging probes, diagnostic agents and contrast agents.

In one embodiment an alginate is employed as the polyuronide. Alginic acid is a linear 1,4-linked block copolymer comprised of β-D-mannuronic acid (M) and α-L-guluronic acid (G) residues. Alginate may come with different mannuronate/guluronate ratios and compositions. Alginates with high G content display the strongest gel-forming ability, based on its diaxial conformation compared to the diequatorial linkage in polyM sequences. Typical M:G ratios for alginates from different biological sources may vary from 1.40–1.95 to 0.45–1.00, with high "G" alginates containing up to 69% G residues compared to ~38–41% for regular alginates. The alginate from brown seaweed *Macrocystis pyrifera*, for instance has 18% polyG segments, 41% polyM segments and 42% mixed G/M segments, whilst *Laminaria hyperborean* alginate has 61% polyG segments, 13% polyM segments and 27% mixed G/M segments. In addition, epimerases may be employed to alter alginate monosaccharides composition. Preferred alginates for use in the present invention are high G alginates having at least about 50% G residues. High G alginates are preferred particularly in applications requiring a gelled form of the alginate, such as beads or capsules derived from the well-known complexation with calcium, barium or similar ions, since they result in higher gel strength or permit gel-formation at lower alginate concentrations. These high G alginates are fluorinated as described herein to make fluorinated high G alginates. When non-gelling alginate compositions are desired, propylene glycol alginates or high M alginates can be employed as starting materials as described herein. Due to their solubility in organic solvents, the propylene glycol alginates are also preferred when the fluorinations involve reagents that are very hydrophobic and incompatible with aqueous solutions. When compositions with no or limited water solubility are desired, alginic acid itself is a preferred starting material or the final product can be converted by appropriate ion exchange processes into the equivalent free alginic acid form. Various other derivatives and variations on the above methods can be used for alginate and other polyuronides that are known to those skilled in the art. Some 200 grades of alginic acid and its various salts are manufactured and are commercially available.

In another embodiment Annexin V is modified for the purposes of the present invention via its N-terminal region in order to fully retain its membrane binding affinity. Suitable modification procedures have been described by Tait et al. (see Tait, J. F., Gibson, D., Fujikawa, K., *J. Bio. Chem.*, 264, 7944–9, 1989; Tanaka, K., Einaga, K. Tsuchiyama, H. Tait, J. F. Fujikawa, K., *Biochemistry*., 35, 922–9, 1996; Tait, J. F., Brown, D. S., Gibson, D., Blankenberg, F. G. Strauss, H. W., *Bioconjugate Chem.*, 11, 918–925, 2000). Analogous procedures can be employed to prepare other bio-active proteins under suitable conditions to retain receptor binding activity. The fluorinated Annexin V is then useful as a diagnostic tool to identify apoptosis in tissues, tumors or other diseased organs and assess the effectiveness of the respective therapeutic interventions.

The paramagnetic compounds of this invention can be used as contrast-enhancing agents for in vivo MR imaging and magnetic resonance angiography. The contrast agents are administered orally, intravascularly or intraperitoneally in physiological buffer or other physiologically acceptable carriers that are well known to one of ordinary skill in the art. The dosage depends on the sensitivity of the NMR imaging instrumentation and on the composition of the contrast agent. Thus, a contrast agent containing a highly paramagnetic substance, e.g., gadolinium (III), generally requires a lower dosage than a contrast agent containing a paramagnetic substance with a lower magnetic moment, e.g., iron (III). In general, dosage will be in the range of about 0.001–1 mmol/kg, more preferably about 0.01–0.1 mmol/kg. In one embodiment, the products are dispersed in a suitable injection medium, such as distilled water or normal saline, to form a dispersion that is introduced into the subject's vascular system by intravenous injection. The particles are then carried through the vascular system to the target organ where they are taken up.

When intravascularly administered, the paramagnetic compounds will be preferentially taken up by organs that ordinarily function to cleanse the blood of impurities, notably the liver, spleen, and lymph nodes, and the other organs that tend to accumulate such impurities, notably bone and neural tissue and to some extent, lung. In each of these organs and tissues, the uptake into the reticuloendothelial cells will occur by phagocytosis, wherein the compounds enter the individual cells in membrane-bound vesicles; this permits a longer half-life in the cells, as such membrane-bound paramagnetic compounds will not tend to clump or aggregate (aggregates are rapidly metabolized and cleared from the organ/tissue). Other uptake mechanisms are possible, e.g., pinocytosis. Also, it is possible that the other cells of the liver (hepatocytes) may absorb the paramagnetic compounds.

Because cancerous tumor cells can lack the ability of phagocytic uptake, the intravascularly administered paramagnetic compounds can serve as valuable tools in the diagnosis of cancer in the above-mentioned organs, as tumors will be immediately distinguishable on any image obtained.

In another embodiment, the paramagnetic compounds are administered as dispersions into the gastrointestinal tract that includes the esophagus, stomach, large and small intestine, either orally, by intubation, or by enema, in a suitable medium such as distilled water or any suitable pharmaceutical vehicle. The particles are preferentially absorbed by the cells of the tract, especially those of the intestine and, like the intravascularly introduced particles will exert an effect on $T_2$ of the organ or tissue. In this manner, cancers and other debilitating diseases of the digestive system such as ulcers can be diagnosed and affected areas pinpointed.

Preparation of New Imaging Probes

The novel fluorinated compounds of the present invention containing a carbohydrate, a polymer or protein backbone or substrate are obtained by treating the respective starting materials (backbone or substrate moiety) with fluorine moieties employing routine fluorination chemistry such as those described below.

New fluorinated polymers are prepared as MRI probes. One target substrate is alginate, which can be fluorinated by a number of processes. A series of such fluorine-containing, water soluble alginates can be prepared with a wide range of fluorine contents. Fluorine contents can vary from 5% to over 40%, and can readily be further maximized. More importantly, although some line broadening of the NMR resonances of the fluorine-containing, water soluble alginates may be observed, their $^{19}$F-NMR spectra may display very high signal to noise (STN) ratios that are of excellent diagnostic value, even at modest fluorine contents. FIG. 1*a* shows the example of a heptafluorobutyryl alginate derivative (Example 1, F ~10%) and its $^{19}$F-NMR spectrum in dilute aqueous solution (~3 w/v %) acquired with only 100 transients. FIGS. 1*a,b* shows the six, well-dispersed (~45 ppm) trifluoromethyl and difluoromethylene resonances of this derivative with high STNs.

Figure 1C:
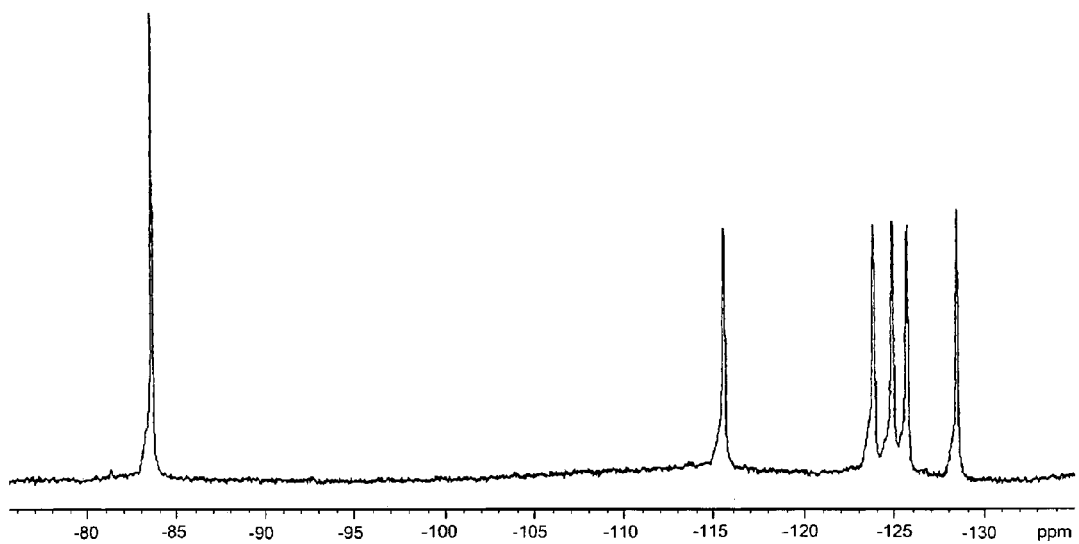
Figure 2A:
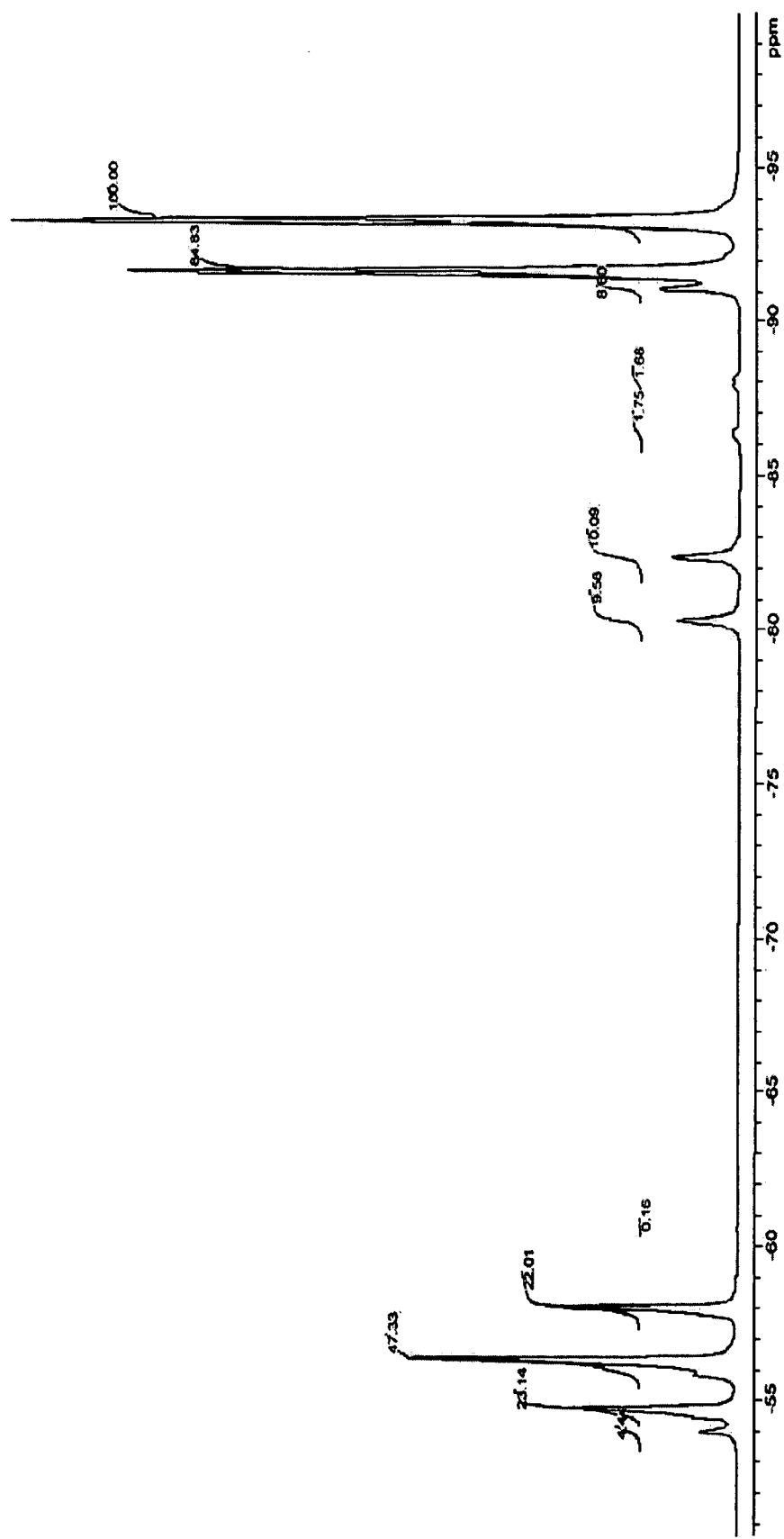
FIGS. 2A–C shows NMR spectra of selected perfluoroalginates: (a) perfluoropolymer alginate derivative of Example 9; (b) perfluorophenylhydrazone alginate derivative of Example 7; and (c) perfluoropolymer alginate derivative of Example 4 (376 MHz $^{19}$F-NMRs (in $D_2O$)).
Figure 2B:
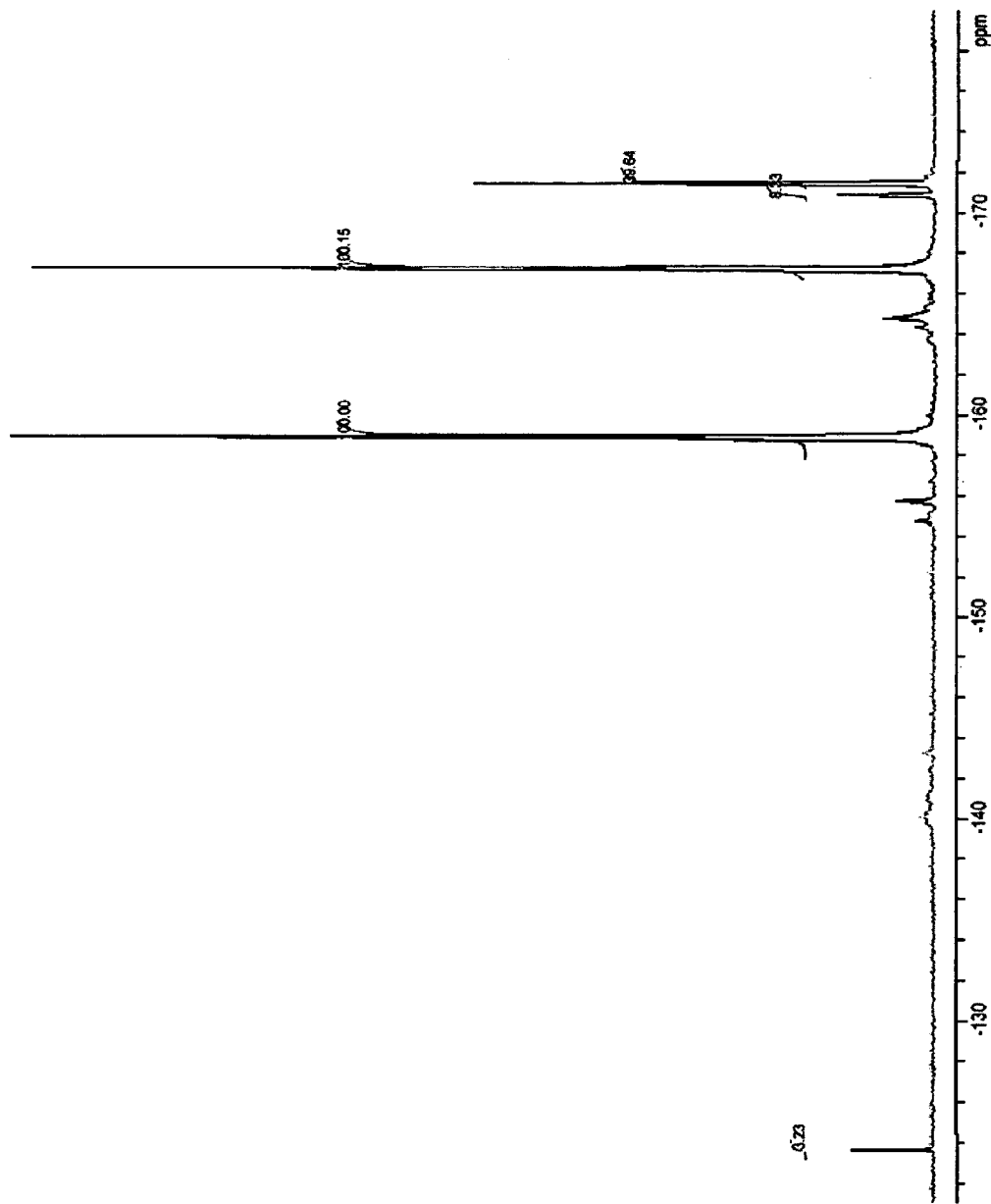
Figure 2C:
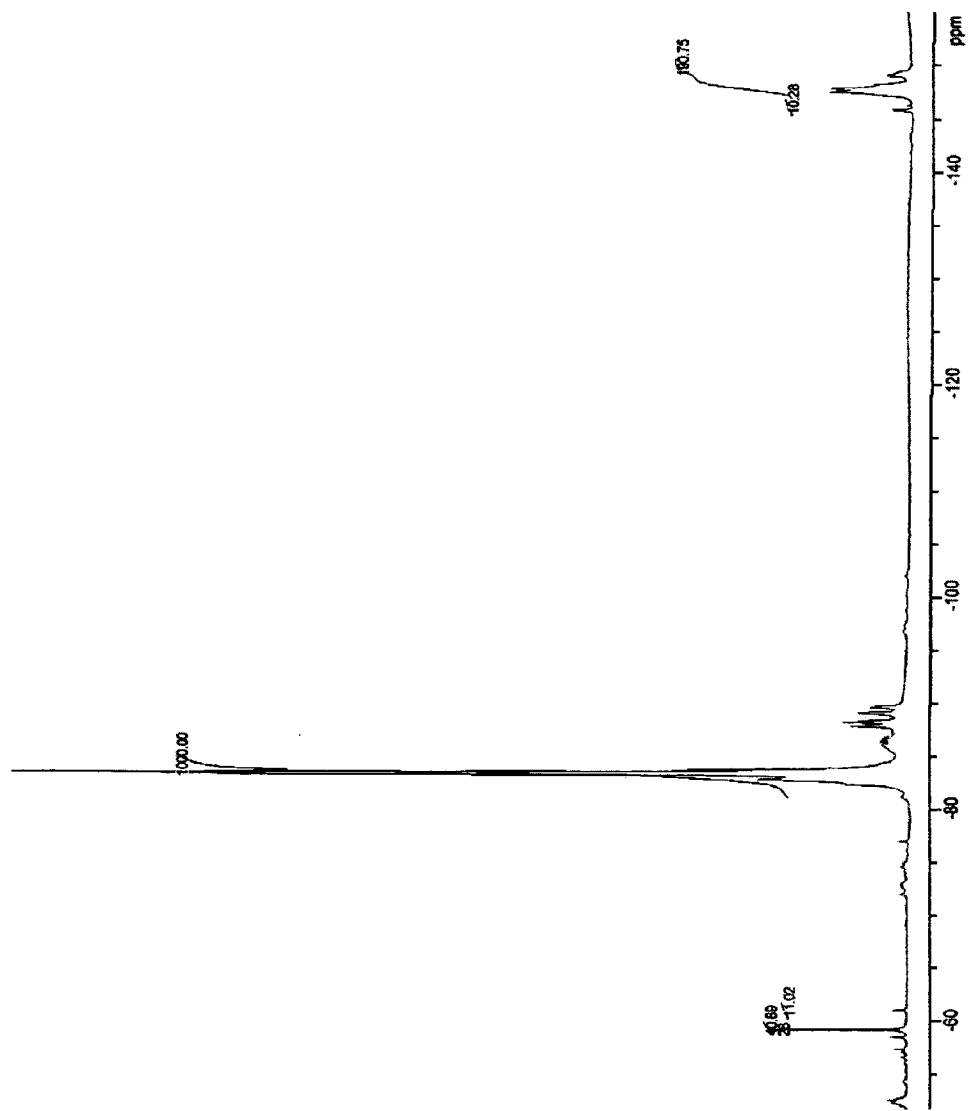

Furthermore, when heptafluorobutyryl alginate was transformed into beads by addition to aqueous calcium solutions, the resulting $^{19}$F-NMR spectrum (FIG. 1*c*) was acceptable, even at the relatively low overall concentrations of this material (0.4%). Various additional examples of these MRI probes were prepared (see Examples 2–17), using alginate and other fluorination approaches. The $^{19}$F-NMR spectra of some of the resulting materials are displayed in FIG. 2. It is evident that in all cases, the alginate probes produce very suitable NMR spectra with high STNs, whose $^{19}$F-resonances could be tailored to appear in a broad range of spectral regions, depending on the type of fluorine residue incorporated. Thus, FIG. 2*c* shows the $^{19}$F-NMR spectrum of the perfluoroaniline alginate derivative of Example 4, with all its major resonances appearing between –150 and –175 ppm. The dominant resonances of the perfluoropolymer alginate derivative of Example 9 (FIG. 2*a*) are at –60 to –80 ppm, and those of the derivative of Example 11 (FIG. 2*b*) are at –55 to –85 ppm, respectively. The ability to tailor spectral properties of polymeric imaging agents by appropriate choice of fluorine substituents offers clear advantages, particularly when MRI experiments require resonances in specific spectral regions for selective pulse sequences. Another benefit is that these new polymeric imaging agents permit the combined use of standard PFCs (e.g., in encapsulated form), without causing concerns for potential spectral overlap of the respective fluorine resonances. Such multiple $^{19}$F probe systems could possibly be designed to facilitate the simultaneous assessment of several environmental conditions.

Linking of fluorinated residues to polyuronides, Annexin V, and other substrates described herein can be accomplished by a number of well known reactions, many of which have been described generally in conjugate chemistry (for reviews see, for instance: G. T. Hermanson, *Bioconjugate Chemistry*, Academic Press, New York, 1996; S. S. Wong, *Chemistry of protein conjugation and cross-linking*, CRC Press, Boca Raton, 1993; R. L. Lundblad, *Techniques in Protein Modification*, CRC Press, Boca Raton, 1994; C. F. Meares (ed.), *Perspectives in Bioconjugate Chemistry*, American Chemical Society, Washington, 1993).

A terminal hydroxyl group on the polyuronides, proteins (Annexin V), and other substrates described herein can be allowed to react with bromoacetyl chloride to form a bromoacetyl ester that in turn is allowed to react with an amine precursor to form the —NH—CH$_2$—C(O)— linkage. A terminal hydroxyl group also can be allowed to react with 1,1'-carbonyl-bisimidazole and this intermediate in turn allowed to react with an amino precursor to form a —NH—C(O)O— linkage (see Bartling et al., *Nature*, 243, 342, 1973). A terminal hydroxyl also can be allowed to react with a cyclic anhydride such as succinic anhydride to yield a half-ester which, in turn, is allowed to react with a precursor of the formula C$_x$F$_y$H$_z$—NH$_2$ using conventional peptide condensation techniques such as dicyclohexylcarbodiimide, diphenylchlorophosphonate, or 2-chloro-4,6-dimethoxy-1,3,5-triazine (see e.g., Means et al., *Chemical Modification of Proteins*, Holden-Day, 1971). A terminal hydroxyl group can also be allowed to react with 1,4-butanediol diglycidyl ether to form an intermediate having a terminal epoxide function linked to the polymer through an ether bond. The terminal epoxide function, in turn, is allowed to react with an amino or hydroxyl precursor (Pitha et al., *Eur. J. Biochem.*, 94, 11, 1979; Elling and Kula, *Biotech. Appl. Biochem.*, 13, 354, 1991; Stark and Holmberg, *Biotech. Bioeng.*, 34, 942, 1989).

Halogenation of a hydroxyl group permits subsequent reaction with an alkanediamine such as 1,6-hexanediamine. The resulting product then is allowed to react with carbon disulfide in the presence of potassium hydroxide, followed by the addition of proprionyl chloride to generate a isothiocyanate that in turn is allowed to react with an amino precursor to yield a —N—C(S)—N—(CH$_2$)$_6$—NH— linkage (see e.g., Means et al., *Chemical Modification of Proteins*, Holden-Day, 1971).

A carboxylic acid group of the polyuronides, proteins (Annexin V), and other substrates described herein can be activated with N,N'-dicyclohexylcarbodiimide, 1-(3-dimethylaminopropyl)-3-ethylcarbodiimide or equivalent carbodiimides and then allowed to react with an amino or hydroxyl group to form an amide or ether respectively. Anhydrides and acid chlorides will produce the same links with amines and alcohols. Alcohols can be activated by carbonyldiimidazole and then linked to amines to produce urethane linkages. Alkyl halides can be converted to amines or allowed to react with an amine, diamines, alcohols, or diol. A hydroxy group can be oxidized to form the corresponding aldehyde or ketone. This aldehyde or ketone then is allowed to react with a precursor carrying a terminal amino group to form an imine that, in turn, is reduced with sodium borohydride or sodium cyanoborohydride to form the secondary amine (see Kabanov et al., *J. Controlled Release*, 22, 141 (1992); *Methods Enzymology*, XLVII, Hirs & Timasheff, Eds., Acad. Press, 1977). The precursor terminating in an amino group can also be allowed to react with an alkanoic acid or fluorinated alkanoic acid, preferably an activated derivative thereof, such as an acid chloride or anhydride, to form a linking group —CONH—. Alternatively, an amino precursor can be treated with an α-ω-diisocyanoalkane to produce an —NC(O)NH(CH$_2$)$_6$NHC(O)—N— linkage (see Means, *Chemical Modification of Proteins*, Holden-Day, 1971). Furthermore, linkages that are unsymmetrical, such as —CONH— or —NHCOO—, can be present in the reverse orientation; e.g., —NHCO— and —OCONH—, respectively. Examples of an activated carbonyl group include anhydride, ketone, p-nitrophenylester, N-hydroxysuccinimide ester, pentafluorophenyl ester and acid chloride.

Suitable fluorinated starting materials for making the novel compositions of the present invention include both organic and inorganic fluorinating agents. Representative fluorinating agents include trifluoromethylhypofluorite, sulfur tetrafluoride, CF$_2$Cl, FSO$_2$[CF$_2$]$_x$CF$_3$ (where x=1–20), potassium fluoride, organic fluorinating agents, such as fluoroamine, fluorocarbamate, fluorotriazine, fluorosulfonylalkyl derivatives, Selectfluor™, fluoroalkylcarboxylic acids, fluoroalkylaldehydes, anhydrides, esters, ketones, acid chlorides of fluoroalkylcarboxylic acids, such as monofluoroacetic acid, difluoroacetic acid, trifluoroacetic acid, pentafluoro-propionic acid, heptafluorobutyric acid, heptafluorobutyric anhydride, heptafluorobutyrylchloride, nonafluoropentanoic acid, tridecafluoroheptanoic acid, pentadecafluorooctanoic acid, heptadecafluorononanoic acid, nonadecafluorodecanoic acid, perfluorododecanoic acid, perfluorotetradecanoic acid; fluoroalkanols, such as 2,2,3,3,4,4,4-heptafluoro-1-butanol, 2,2,3,3,4,4,5,5,6,6,7,7,8,8,8-penta-decafluoro-1-octanol, 2,2,3,3,4,4,5,5,6,6,7,7,8,9,9,9-hepta-decafluoro-1-nonanol, 2,2,3,3,4,4,5,5,6,6,7,7,8,8,9,9,10,10,10-nonadeca-fluoro-1-decanol, Krytox and Zonyl derivatives, fluoroarylesters, fluoroalkylamines, fluoroarylamines, 2,2,3,3,4,4,5,5,6,6,7,7,8,8,9,9,10,10,11,11,11-heneicosafluoro-1-undecanol; fluorinated polymers containing reactive terminal groups, fluoroalkyl halides, such as perfluoroethyl iodide, perfluoropropyl iodide, perfluorohexyl bromide, perfluoroheptyl bromide, perfluorooctyl bromide, perfluorodecyl iodide, perfluorooctyl iodide, 1,1,1,2,2,3,3,4,4,5,5,6,6,7,7,8,8-heptadecafluoro-10-iododecane, 1,1,1,2,2,3,3,4,4,5,5,6,6,7,7,8,8-heptadecafluoro-10-iododecane, polytetrafluoro-ethyleneoxide-co-difluoromethyleneoxide-α,ω-bis(methylcarboxylate), dihydroxypropanoxymethyl derivatives of perfluoropolyoxyalkane, hydroxypolyethylenoxy derivatives of perfluoropolyoxyalkane and the like. Suitable modification procedures have been described in several monographs (J. J. Clark, D. Walls. T. W. Bastock, *Aromatic Fluorination*, CRC Press, Boca Raton, Fla., 1996; M. Hudlicky, A. E. Pavlath, *Chemistry of Organic Fluorine Compounds*, ACS, Washington, D.C. 1995; M. Howe-Grant ed., *Fluorine Chemistry, A Comprehensive Treatment*, Wiley, New York, 1995; G. A. Olah, G. K. Sarya Prakash, R. D. Chambers, eds. *Synthetic Fluorine Chemistry*, Wiley, New York, 1992).

Specific examples of compounds of formulas I–IV may require the use of protecting or blocking groups to enable their successful elaboration into the desired structure. Protecting groups may be chosen with reference to Greene, T. W., et al., *Protective Groups in Organic Synthesis*, John Wiley & Sons, Inc., 1991. The blocking groups are readily removable, i.e., they can be removed, if needed, by procedures that will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

Paramagnetic polyuronides can be prepared by contacting an appropriate salt forming polyuronide with an equimolar amount of an appropriate metal ion under conditions sufficient to form a polyuronide salt. For example, paramagnetic alginate beads can be formed by slowly adding sodium alginate having a high guluronic acid content (>50%) to a stirred aqueous solution of gadolinium (III) acetate at about an equal molar ratio, or at an appropriate different ratio, depending on the end use. The resulting beads that are formed are isolated by centrifugation and can be washed with calcium chloride to remove excess gadolinium. Similarly, superparamagnetic polyuronide beads can be prepared employing the same procedures described above but substituting a suspension of superparamagnetic nanoparticles, such as, iron oxide particles, for the aqueous gadolinium.

Superparamagnetic protein conjugates are prepared by mixing superparamagnetic nanoparticles with a buffered protein solution. The superparamagnetic nanoparticles can optionally be oxidized prior to the reaction with the protein. The reaction mixture is then centrifuged and the supernatant is discarded to give the desired protein conjugate.

The compounds of the present invention can be prepared readily according in the following detailed examples using readily available starting materials, reagents and conventional synthetic procedures. Additional variants are also possible that are known to those of ordinary skill in this art, but that are not mentioned in greater detail. The following examples illustrate the practice of the present invention but should not be construed as limiting its scope.

Materials

Alginic acid, sodium alginate, high G alginate, propyleneglycol alginate 3,5,5'-tris(trifluoromethyl) octafluorohexanoic acid, 3,5,5'-tris(trifluoromethyl) octafluorohexanoic acid, 3,5,5'-tris(trifluoromethyl) octafluorohexanol, perfluoro-3,6,9-trioxatridecanoic acid methyl ester, methyl perfluorohexadecanoate, dextran, poly(ethylene glycol), and superparamagnetic iron oxide nanoparticles (3 nm) were obtained from CarboMer, Inc., Westborough, Mass. and San Diego, Calif.; the alginic acid, sodium alginate, high G alginate, propyleneglycol alginate starting materials had molecular weights of ~600,000, ~500,000, ~450,000, and ~700,000 Da, respectively. The hexafluoropropane oxide and heptafluorobutyryl chloride were obtained from Lancaster Synthesis, Windham, N.H. Deoxo-Fluor [bis(2-methoxyethyl)aminosulfur trioxide] was obtained from Air Products, Allentown, Pa. Polytetrafluoroethyleneoxide-co-difluoromethyleneoxide-α,ω-bisdifluoroacetic acid, gadolinium (III) acetate, polytetrafluoroethyleneoxide-co-difluoromethyleneoxide-α,ω-bis(methylcarboxylate), polytetrafluoroethyleneoxide-co-difluoromethyleneoxide-α,ω-diisocyanate and Annexin V were obtained from Aldrich, St. Louis, Mo.

The formulas in the following examples and claims include m and n subscripts which are included to designate the ratio of repeating units. In each formula the sum of m and n is one (1), ie m+n=1.

EXAMPLE 1

Heptafluorobutyryl Alginic Acid

A solution of heptafluorobutyryl chloride in DMSO (0.6 equivalents) was added to alginic acid and stirred at ambient temperature for 6 hours. The product was precipitated with acetone, filtered, washed with acetone, dialyzed and dried, yielding heptafluorobutyryl alginic acid with F 9.07%.

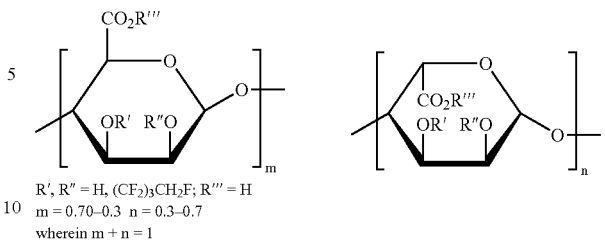

R', R'' = H, $(CF_2)_3CH_2F$; R''' = H
m = 0.70–0.3  n = 0.3–0.7
wherein m + n = 1

R', R''=H,$(CF_2)_3CH_2F$; R'''=H
m+0.70–0.3 n=0.3–0.7 wherein m+n=1
Biocompatibility results heptafluorobutyryl alginate (Example 1) was tested in human cell culture and found to be non-toxic at concentrations of 0.2–1.0%.

EXAMPLE 2

6-[3-[2-(Perfluorohexyl)-2-ethoxy]-2-hydroxypropyl] Alginic Acid

A solution of 3-[2-(perfluorohexyl)-2-ethoxy]-1,2-epoxypropane in methylene chloride (0.6 equivalents) was added to alginic acid and stirred at ambient temperature for 6 hours.

The suspension was filtered, washed with methylene chloride and acetone, dialyzed and dried, yielding 3-[2-(perfluorohexyl)-2-hydroxy] alginate with F 20.41%.

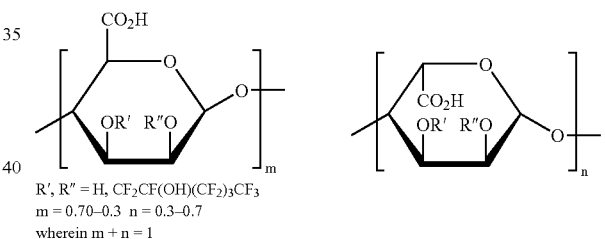

R', R'' = H, $CF_2CF(OH)(CF_2)_3CF_3$
m = 0.70–0.3  n = 0.3–0.7
wherein m + n = 1

EXAMPLE 3

Perfluoro tri-n-butylamine Alginate

A solution of perfluoro tri-n-butylamine in water (1.1 equivalents) was added to alginic acid and stirred at ambient temperature for 6 hours. The product was precipitated with acetone, filtered, washed with acetone, dialyzed and dried, yielding perfluoro tri-n-butylamine alginate with F 9.41%

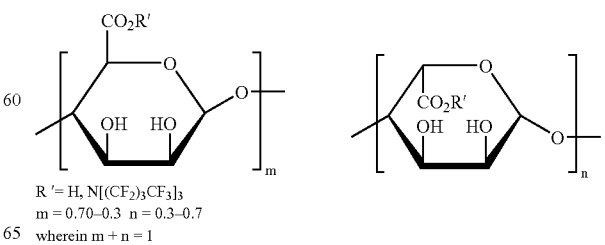

R' = H, $N[(CF_2)_3CF_3]_3$
m = 0.70–0.3  n = 0.3–0.7
wherein m + n = 1

EXAMPLE 4

Poltetrafluoroethyleneoxide-co-difluoromethyleneoxide-α-methyl-carboxylate-ω-carboxylate Propylene Glycol Alginate A solution of propylene glycol alginate in methanol was treated with polytetrafluoroethyleneoxide-co-difluoromethyleneoxide-α,ω-bis(methylcarboxylate) (Mw ~2,000 Da, 0.6 equivalents) and the resulting viscous paste was stirred at ambient temperature for 6 hours. The reaction mixture was precipitated with acetone, washed with acetone, filtered, dialyzed and dried, yielding the perfluoropolymer-labeled alginate with F 27.66%.

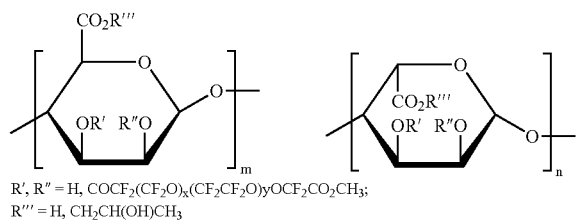

R', R" = H, COCF$_2$(CF$_2$O)$_x$(CF$_2$CF$_2$O)$_y$OCF$_2$CO$_2$CH$_3$;
R''' = H, CH$_2$CH(OH)CH$_3$ m+0.70–0.3 n=0.3–0.7 wherein m+n=1

EXAMPLE 5

6-[2-(Perfluorohexyl)-2-hydroxy] DANSYL Alginic Acid

A solution of 6-[2-(perfluorohexyl)-2-hydroxy] alginate (Example 2, 0.6 equivalents) in DMSO was treated with 5-N,N-dimethylamino-1-naphthalensulfonyl (DANSYL) chloride (0.1 equivalents) dissolved in dry acetone and sodium carbonate (0.1 equivalents) and stirred at ambient temperature for 3 hours. The reaction mixture was precipitated with acetone, washed with acetone, filtered, dialyzed and dried, yielding Dansylated 6-[2-(perfluorohexyl)-2-hydroxy] alginate.

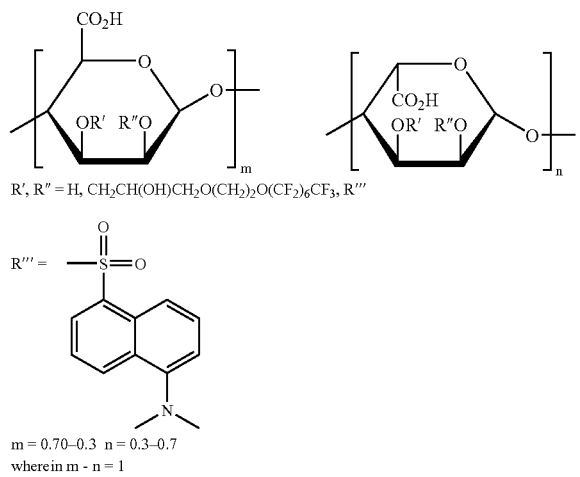

R', R" = H, CH$_2$CH(OH)CH$_2$O(CH$_2$)$_2$O(CF$_2$)$_6$CF$_3$, R''' m = 0.70–0.3 n = 0.3–0.7
wherein m - n = 1

EXAMPLE 6

3-[(Hexafluoropropyl)-2-hydroxy] Alginic Acid

A solution of hexafluoropropyleneoxide in methylene chloride (0.8 equivalents) was added to sodium alginate with high guluronic acid content (68%) and stirred at ambient temperature for 6 hours. The suspension was filtered, washed with methylene chloride and acetone, dialyzed and dried, yielding 3-[(hexafluoropropyl)-2-hydroxy] alginate with F 12.50%.

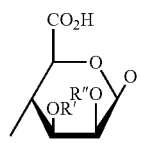

EXAMPLE 7

Perfluorophenylhydrazone Alginic Acid

A solution of perfluorophenylhydrazine in methylene chloride (0.6 equivalents) was added to an aqueous solution of sodium alginate with high guluronic acid content (68%) and stirred at ambient temperature for 6 hours. The reaction mixture was precipitated with acetone, washed with acetone, filtered, dialyzed and dried, yielding perfluorophenylhydrazone alginate with F 10.35%.

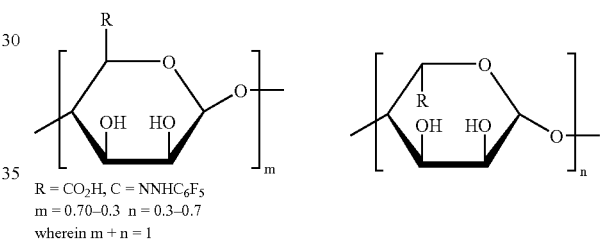

R = CO$_2$H, C = NNHC$_6$F$_5$
m = 0.70–0.3 n = 0.3–0.7
wherein m + n = 1

EXAMPLE 8

Polytetrafluoroethyleneoxide-co-difluoromethyleneoxide-α-difluoroacetic acid-ω-difluoroacetyl Fluorescein Alginate An aqueous solution of sodium alginate with high guluronic acid content (68%) was treated with polytetrafluoroethyleneoxide-co-difluoromethyleneoxide-α,ω-bisdifluoroacetic acid (Mw ~500, 0.6 equivalents) and the resulting viscous paste was stirred at ambient temperature for 6 hours. A portion was treated with fluorescein isothiocyanate (0.1 equivalents) for 4 hours. The reaction mixture was precipitated with acetone, washed with acetone, filtered, dialyzed and dried, yielding perfluoropolymer- and FITC-labeled alginate with F 22.64%.

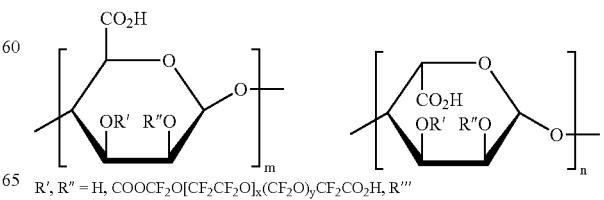

R', R" = H, COOCF$_2$O[CF$_2$CF$_2$O]$_x$(CF$_2$O)$_y$CF$_2$CO$_2$H, R'''

-continued

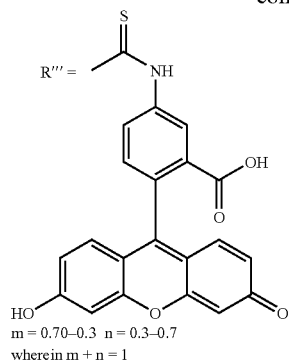

m = 0.70–0.3  n = 0.3–0.7
wherein m + n = 1

EXAMPLE 9

Polytetrafluoroethyleneoxide-co-difluoromethyl-eneoxide-α-difluoroacetic acid-ω-difluoroacetyl Propylene Glycol Alginate A solution of propylene glycol alginate in methanol was treated with polytetrafluoroethyleneoxide-co-difluoromethyleneoxide-α,ω-bisdifluoroacetic acid (Mw ~2,000, 0.6 equivalents) and the resulting viscous paste was stirred at ambient temperature for 6 hours. The reaction mixture was precipitated with acetone, washed with acetone, filtered, dialyzed and dried, yielding perfluoropolymer-labeled alginate with F 33.04%.

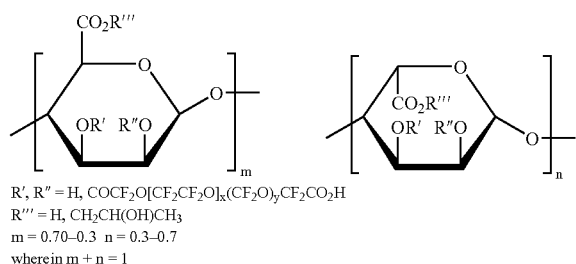

R', R" = H, COCF$_2$O[CF$_2$CF$_2$O]$_x$(CF$_2$O)$_y$CF$_2$CO$_2$H
R''' = H, CH$_2$CH(OH)CH$_3$
m = 0.70–0.3  n = 0.3–0.7
wherein m + n = 1

EXAMPLE 10

Perfluorobenzamide Alginate

A solution of perfluoroaniline (0.6 equivalents) in methylene chloride was added to an aqueous solution of sodium alginate with high guluronic acid content (68%) and stirred at ambient temperature for 6 hours. The reaction mixture was precipitated with acetone, washed with acetone, filtered, dialyzed and dried, yielding perfluorobenzamide alginate with F 19.35%.

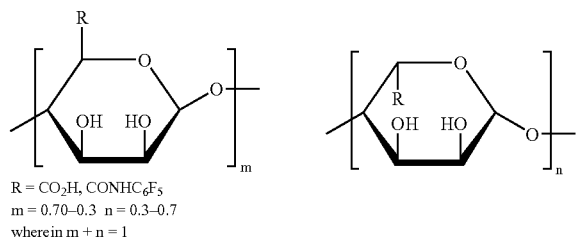

R = CO$_2$H, CONHC$_6$F$_5$
m = 0.70–0.3  n = 0.3–0.7
wherein m + n = 1

EXAMPLE 11

Perfluoroaniline Alginate

A solution of perfluoroaniline (0.6 equivalents) in methylene chloride was added to an aqueous solution of aqueous sodium alginate with high guluronic acid content (68%). Sodium cyanoborohydride (8.6 equivalents) was added and stirred at ambient temperature for 6 hours. The reaction mixture was precipitated with acetone, washed with acetone, filtered, dialyzed and dried, yielding perfluoroaniline alginate with F 22.65%.

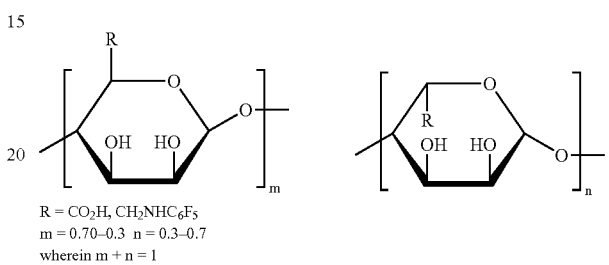

R = CO$_2$H, CH$_2$NHC$_6$F$_5$
m = 0.70–0.3  n = 0.3–0.7
wherein m + n = 1

EXAMPLE 12

3-[(Hexafluoropropyl)-2-hydroxy] Propyleneglycol Alginate

A solution of hexafluoropropyleneoxide in methylene chloride (0.7 equivalents) was added to propyleneglycol alginate and stirred at ambient temperature for 6 hours. The suspension was filtered, washed with methylene chloride and acetone, dialyzed and dried, yielding 3-[(hexafluoropropyl)-2-hydroxy]propyleneglycol alginate with F 20.41%.

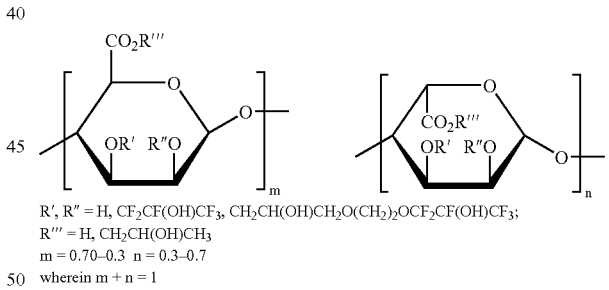

R', R" = H, CF$_2$CF(OH)CF$_3$, CH$_2$CH(OH)CH$_2$O(CH$_2$)$_2$OCF$_2$CF(OH)CF$_3$;
R''' = H, CH$_2$CH(OH)CH$_3$
m = 0.70–0.3  n = 0.3–0.7
wherein m + n = 1

EXAMPLE 13

Polytetrafluoroethyleneoxide-co-difluoromethyl-eneoxide-α-tolylurethane-ω-tolylisocyanate Propylene Glycol Alginate A solution of propylene glycol alginate in methanol was treated with polytetrafluoroethyleneoxide-co-difluoromethyleneoxide-α,ω-diisocyanate (Mw ~3,000, 0.6 equivalents) and the resulting viscous paste was stirred at ambient temperature for 6 hours. The reaction mixture was precipitated with acetone, washed with acetone, filtered, dialyzed and dried, yielding perfluoropolymer-labeled alginate with F 29.99%.

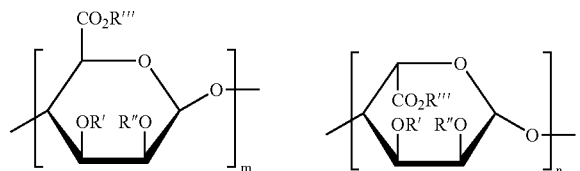

R', R″ = H, ⎯NHCOC$_6$H$_3$[CH$_3$]NHCO$_2$[CF$_2$CF$_2$O]$_k$(CF$_2$O)$_y$CONHC$_6$H$_3$(NCO)CH$_3$;
R‴ = H, CH$_2$CH(OH)CH$_3$
m = 0.70–0.3  n = 0.3–0.7
wherein m + n = 1

EXAMPLE 14

Perfluoro-3,6,9-trioxatridecanoate Alginate

An aqueous solution of alginate with high guluronic acid content (68%) was treated with perfluoro-3,6,9-trioxatridecanoic acid methyl ester (1.6 equivalents) and the resulting viscous paste was stirred at ambient temperature for 16 hours. The reaction mixture was precipitated with acetone, washed twice with acetone, filtered, dialyzed and dried, yielding perfluoro-3,6,9-trioxatridecanoate alginate with F 30.25%.

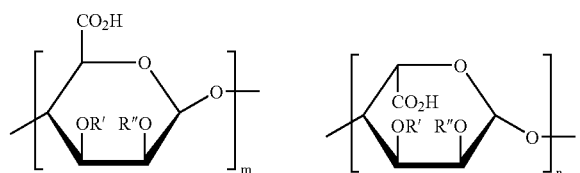

R', R″ = H, COCF$_2$O(CF$_2$)$_2$O(CF$_2$)$_2$O(CF$_2$)$_3$CF$_3$
m = 0.70–0.3  n = 0.3–0.7
wherein m + n = 1

EXAMPLE 15

3,5,5'-Tris(trifluoromethyl)octafluorohexanoate Alginate

A dispersion of alginate with high guluronic acid content (68%) in acetone was treated with 1,3-diisopropylcarbodiimide (0.8 equivalents) for 1 hour and then with 3,5,5'-tris (trifluoromethyl) octafluorohexanol (0.6 equivalents) and the resulting viscous Paste was stirred at ambient temperature for 16 hours. The reaction mixture was precipitated with acetone, washed twice with acetone, filtered, dialyzed and dried, yielding the perfluoro-3,5,5'-trimethylhexanoate alginate with F 24.73%.

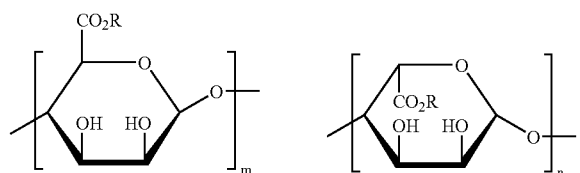

R = H, COCF$_2$CF(CF$_3$)CF$_2$C(CF$_3$)$_3$
m = 0.70–0.3  n = 0.3–0.7
wherein m + n = 1

EXAMPLE 16

3,5,5'-Tris(trifluoromethyl)octafluorohexanoate Propylene Glycol Alginate

A solution of propylene glycol alginate in methanol was treated with 3,5,5'-tris(trifluoromethyl)octafluorohexanoic acid (0.4 equivalents) and the resulting viscous paste was stirred at ambient temperature for 16 hours. The reaction mixture was precipitated with acetone, washed twice with acetone, filtered, dialyzed and dried, yielding the perfluoro-3,5,5'-trimethylhexanoate-labeled alginate with F 14.71%.

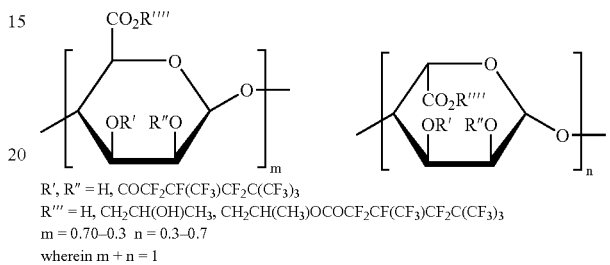

R', R″ = H, COCF$_2$CF(CF$_3$)CF$_2$C(CF$_3$)$_3$
R‴ = H, CH$_2$CH(OH)CH$_3$, CH$_2$CH(CH$_3$)OCOCF$_2$CF(CF$_3$)CF$_2$C(CF$_3$)$_3$
m = 0.70–0.3  n = 0.3–0.7
wherein m + n = 1

EXAMPLE 17

Methyl Perfluorohexadecanoate Alginate

An aqueous solution of alginate with high guluronic acid content (68%) was treated with methyl perfluorohexadecanoate (0.4 equivalents) and the resulting viscous paste was stirred at ambient temperature for 16 hours. The reaction mixture was precipitated with acetone, washed twice with acetone, filtered, dialyzed and dried, yielding the methyl perfluorohexadecanoate alginate with F 32.36%.

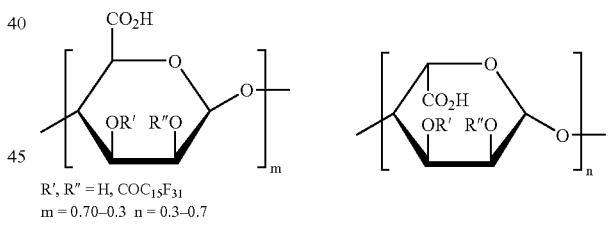

R', R″ = H, COC$_{15}$F$_{31}$
m = 0.70–0.3  n = 0.3–0.7
wherein m + n = 1

EXAMPLE 18

Paramagnetic Gadolinium Alginate Beads

To a rapidly stirred, aqueous solution of gadolinium (III) acetate (1.1 equivalents) was added dropwise a dilute aqueous solution of sodium alginate with high guluronic acid content (68%) through a syringe. The resulting gel beads were centrifuged, the supernatant was discarded, and the beads were washed and centrifuged twice with dilute calcium chloride solution to remove excess gadolinium. A magnetization curve revealed that the alginate beads were paramagnetic. Sterile preparations were obtained, by filter sterilizing the component solutions through 0.22 micron filters prior to their combination. Paramagnetic gadolinium alginate beads (Example 18) were found to be non-toxic in cell culture.

EXAMPLE 19

Superparamagnetic Iron Oxide Alginate Beads

To a rapidly stirred suspension of superparamagnetic iron oxide nanoparticles (3 nm, 1.1 equivalents) in a 10 mmol aqueous calcium chloride solution containing poly(ethylene glycol) (NF grade, Mw 400, 25%) was added dropwise with a syringe to a dilute aqueous solution of sodium alginate with high guluronic acid content (68%). The resulting gel beads were centrifuged, the supernatant was discarded, and the beads were washed and centrifuged twice with dilute calcium chloride solution. A magnetization curve revealed that the alginate beads were superparamagnetic. Sterile preparations were obtained by filter sterilizing the component solution and suspension through 0.22 micron filters prior to their combination.

EXAMPLE 20

Superparamagnetic Iron Oxide Alginate-coated Nanoparticles

To a rapidly stirred, 10 mmol aqueous calcium chloride solution was added dropwise through a syringe a suspension of superparamagnetic iron oxide nanoparticles (3 nm) in a dilute aqueous solution of sodium alginate with high guluronic acid content (68%). The resulting coated nanoparticles were centrifuged, the supernatant was discarded, and the nanoparticles were washed and centrifuged twice with dilute calcium chloride solution.

EXAMPLE 21

Superparamagnetic Iron Oxide Alginate-coated Nanoparticles

To a rapidly stirred, dilute aqueous solution of sodium alginate with high guluronic acid content (68%) was slowly added a suspension of superparamagnetic iron oxide nanoparticles (3 nm) in a poly(ethylene glycol) (NF grade, Mw 400, 25%). The resulting suspension was stirred for 10 minutes, then heated for 30 minutes at 70° C. and centrifuged. The supernatant was discarded, and the coated nanoparticles were dialyzed.

EXAMPLE 22

Superparamagnetic Iron Oxide Dextran-coated Nanoparticles

To a rapidly stirred, dilute aqueous dextran (Mw 10,000) solution was slowly added a suspension of superparamagnetic iron oxide nanoparticles (3 nm) in a poly(ethylene glycol) (NF grade, Mw 400, 25%). The resulting suspension was stirred for 10 minutes, then heated for 30 minutes at 70° C. and centrifuged The supernatant was discarded, and the coated nanoparticles were dialyzed.

EXAMPLE 23

Superparamagnetic Iron Oxide Annexin Conjugate

To a rapidly stirred, aqueous solution of superparamagnetic iron oxide dextran-coated nanoparticles from Example 22 was added sodium paraperiodate (0.05 equivalents) and the resulting mixture was stirred for 1 h. Ethylene glycol was added and the mixture was then centrifuged. The supernatant was discarded, and the oxidized, coated nanoparticles were washed and centrifuged twice with PBS buffer. The oxidized, coated nanoparticles were added to a buffered solution of Annexin V. The resulting mixture was stirred for 25 minutes at 4° C. and then centrifuged. The supernatant was discarded, to give the desired conjugate.

EXAMPLE 24

Superparamagnetic Iron Oxide Annexin Conjugate

Following the procedure outlined for Example 23, alginate-coated nanoparticles prepared according to Examples 20 or 21 were used either with the oxidation step, or directly, to give the desired conjugates.

EXAMPLE 25

Fluorescent, Superparamagnetic Iron Oxide Annexin Conjugate

Following the procedure outlined for Examples 22 and 23, fluorescein isocyanate labeled Annexin V was used instead of the unlabeled protein to give the desired fluorescent conjugates with coated superparamagnetic iron oxide nanoparticles. Alternatively, fluorescent alginate (e.g., Examples 5 and 8) could be employed.

EXAMPLE 26

Heptafluorobutyryl Hydroxyethyl Starch

A solution of heptafluorobutyryl chloride in DMSO (0.6 equivalents) was added to hydroxyethyl starch and stirred at ambient temperature for 12 hours. The product was precipitated with acetone, filtered, washed with acetone, dialyzed and dried, yielding heptafluorobutyryl hydroxyethyl starch with F 16.75%.

EXAMPLE 27

Perfluorotri-n-butylamine Alginate

An aqueous acidic dispersion of alginic acid was treated with perfluorotri-n-butylamine (1.6 equivalents) at ambient temperature for 12 hours. The product was precipitated with alcohol, filtered, washed with acetone, dialyzed and dried, yielding perfluorotri-n-butylamine alginate with F 11.50%.

Uses of Novel Imaging Agents

The fluorinated polyuronides and in particular the fluorinated alginates of the present invention display sensitivity in their $T_1$. relaxation times to different oxygen partial pressures ($pO_2$), producing linear correlation over a range of $pO^2$. This demonstrates their utility as oxygen sensitive imaging probes. The fluorinated alginates also display chemical shift and temperature sensitivity, indicating their utility as temperature sensitive imaging probes. These novel agents of this invention are suitable for many diagnostic uses, and provide the ability to image in vivo or non-invasively monitor tissues, organs and cellular implants, for example, pancreatic islet β-cells that are encapsulated with the present fluorinated polyuronides, and measure their mass, function, viability or evidence of inflammation. Additionally, engraftment of transplanted isolated pancreatic islets can be monitored, using, for example, islets labeled with β-cell specific oxygen-sensitive fluorinated probes. $^{19}$F-MRI with these novel agents permits monitoring of other disorders, such as cancer, the comparison of normal or diseased cells, organs or tissues, the viability of transplanted cells or other tissues when those fluorinated agents have specificity for target tissues. This new methodology is instrumental in the development of clinical examinations for monitoring disease progress and response to therapy in diabetics and in people strongly at risk for diabetes and other patient populations.

The simultaneous incorporation of $^{19}$F or superparamagnetic residues and fluorescent moieties into the polyuronides or polymeric agents affords diagnostic probes that can be employed for both MRI and fluorescent studies. Examples of such dual function diagnostic probes are those polyuronides or proteins that contain both a fluorine moiety as described herein and a fluorescent moiety or a fluorinated fluorescent moiety such as: 4-trifluoromethyl-7-aminocoumarin, 4-trifluoromethyl-umbelliferone (or its acetate or butyrate derivatives), 4-fluoro-7-sulfamyl-benzofurazam, certain BODIPY dyes, e.g., N-(4,4'-difluoro-5,7-dimethyl-4-bora-3a,4a-diaza-s-indacene-3-yl)-methyliodoacetamide, N-(4,4'-difluoro-1,3,5,7-tetramethyl-4-bora-3a,4a-diaza-s-indacene-2-yl)-iodoacetamide and 4,4'-difluoro-5-phenyl-4-bora-3a,4a-diaza-s-indacene-3-propionic acid, 3-chloro-1-(3-chloro-5-(trifluoromethyl)-2-pyridimyl)-5-(trifluoromethyl)-2[1H]-pyridinone, 6-carboxymethylthio-2',4',5',7'-tetrabromo-4,5,7-trifluorofluorescein (Eosin F3S), and Oregon Green carboxylic acid.

All patents, patent applications, provisional applications, and publications referred to or cited herein are incorporated by reference in their entirety, including all figures and tables, to the extent they are not inconsistent with the explicit teachings of this specification.

REFERENCES

1. U.S. Pat. No. 6,019,959 Feb. 1, 2000 Oligomeric compounds that contain perfluoroalkyl, process for their production, and their use in NMR diagnosis
   INVENTOR(S)—Platzek, Johannes; Niedballa, Ulrich; Raduchel, Bernd; Schlecker, Wolfgang; Weinmann, Hanns-Joachim; Frenzel, Thomas; Misselwitz, Bernd; Ebert, Wolfgang
   PATENT ASSIGNEE(S)—Schering Aktiengesellschaft
2. U.S. Pat. No. 6,011,048 dated Jan. 4, 2000 Thiazole benzenesulfonamides as β3 agonists for treatment of diabetes and obesity
   INVENTOR(S)—Mathvink; Robert J.; Parmee; Emma R.; Tolman; Samuel; Weber; Ann E.
   PATENT ASSIGNEE(S)—Merck & Co., Inc.
3. U.S. Pat. No. 5,510,496 dated Apr. 23, 1996 Substituted pyrazolyl benzenesulfonamides
   INVENTOR(S)—Talley; John J.; Penning; Thomas D.; Collins; Paul W.; Malecha; James W.; Bertenshaw; Stephen R.; Graneto; Matthew J.
   PATENT ASSIGNEE(S)—G. D. Searle & Co.
4. U.S. Pat. No. 5,342,823 dated Aug. 30, 1994 Sulfonylureas
   INVENTOR(S)—Kuhlmeyer; Rainer; Topfl; Werner; Fory; Werner
   PATENT ASSIGNEE(S)—Ciba-Geigy Corporation
5. U.S. Pat. No. 6,218,464 dated Apr. 17, 2001 Preparation of fluorinated polymers
   INVENTOR(S)—Parker; Hsing-Yeh; Lau; Willie; Rosenlind; Erik S.
   PATENT ASSIGNEE(S)—Rohm and Haas Company
6. U.S. Pat. No. 5,798,406 dated Aug. 25, 1998 Fluorinated acrylic and methacrylic latices and mixtures thereof, processes for manufacturing them and their applications in the field of hydrophobic coatings
   INVENTOR(S)—Feret; Bruno; Sarrazin; Laure; Vanhoye; Didier
   PATENT ASSIGNEE(S)—Elf Atochem S. A
7. PCT WO 00/40252, dated 2000 Hetero-polysaccharide conjugate and methods of making and using the same
   INVENTOR(S)—C. Fraker, L. Invaeradi, M. Mares-Guia, C. Ricordi
   PATENT ASSIGNEE(S)—Biomm, Inc. & University of Miami

I claim:

1. A fluorinated or paramagnetic polyuronide polymer comprising a polymer of Formula I, II, III or IV

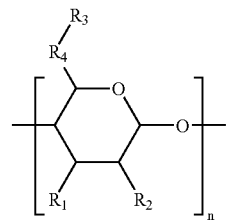

I

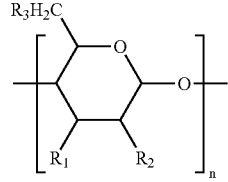

II

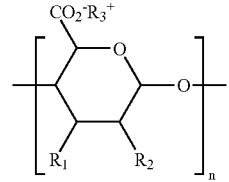

III

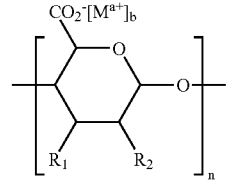

IV and pharmaceutically acceptable salts thereof for the polymers that are capable of forming salts,
wherein
for Formula I:
$R_1$ represents OH, OX, X; $R_2$ represents OH, OX, X; $R_3$ represents OH, OY, OX, NHX, alkyl, alkoxyalkyl; $R_4$ represents C=O, $CH_2$, CNX, $CF_2$;
for Formula II:
$R_1$ represents OH, OX, X, $OR_4$; $R_2$ represents OH, OX, X, OR4; $R_3$ represents OH, Y, X; $R_4$=acyl, alkyl or aryl
for Formula III:

$R_1$ represents OH, OX, X; $R_2$ represents OH, OX, X; $R_3$ represents H, $N(X)_3$;

for Formula IV:

$R_1$ represents OH, OX, X; $R_2$ represents OH, OX, X, —OA(X)O— or $OA(R_5)O$—; $R_5$ represents alkyl or acyl and A represents a non-paramagnetic ion wherein M is any paramagnetic ion of the transition metal or lanthanide series, and "a" is a whole number and "b" is 1/a;

wherein for all of the formulas I–IV

X represents a fluorine containing moiety;

Y represents $CH_2C(OH)CH_3$;

m, p, x, y, z represents 0–150; and n is from 10–10,000 inclusive.

2. The polyuronide polymer, according to claim 1, comprising a compound selected from the group consisting of a. heptafluorobutyryl alginic acid of the formula

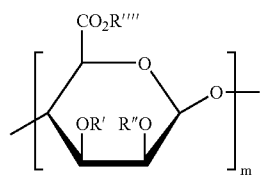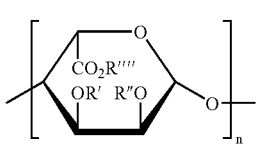

R', R" = H, $(CF_2)_3CH_2F$; R''' = H
wherein m + n = 1 b. 6-[3-[2-(perfluorohexyl)-2-ethoxy]-2-hydroxypropyl] alginic acid of the formula

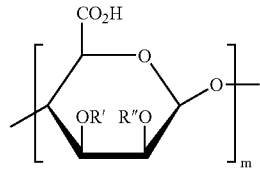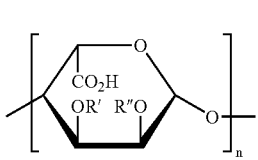

R', R" = H, $CF_2CF(OH)(CF_2)_3CF_3$
wherein m + n = 1 c. perfluoro tri-n-butylamine alginate of the formula

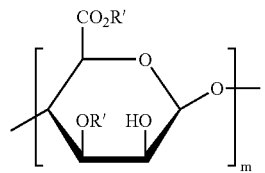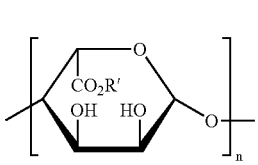

R', R" = H, $N[(CF_2)_3CF_3]_3$
wherein m + n = 1 d. polytetrafluoroethyleneoxide-co-difluoromethyleneoxide-α-methyl-carboxylate-ω-carboxylate propylene glycol alginate of the formula

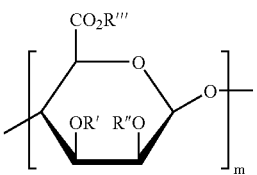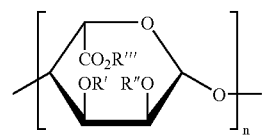

R', R" = H, $COCF_2(CF_2O)_x(CF_2CF_2O)_yOCF_2CO_2CH_3$;
R''' = H, $CH_2CH(OH)CH_3$
wherein m + n = 1 e. 6-[2-(Perfluorohexyl)-2-hydroxy] DANSYL alginic acid of the formula

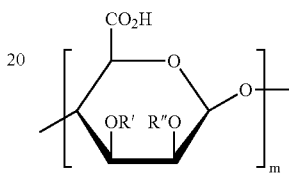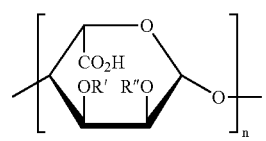

R', R" = H, $CH_2CH(OH)CH_2O(CH_2)_2O(CF_2)_6CF_3$, R''' =

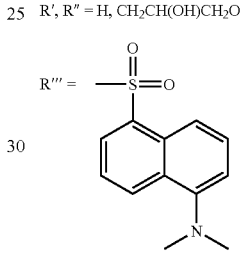

wherein m + n = 1 f. 3-[(hexafluoropropyl)-2-hydroxy] alginic acid of the formula

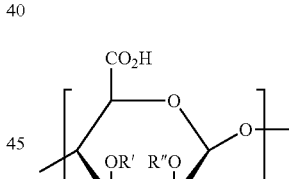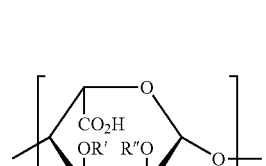

R', R" = H, $CF_2CF(OH)CF_3$
wherein m + n = 1 g. perfluorophenylhydrazone alginic acid of the formula

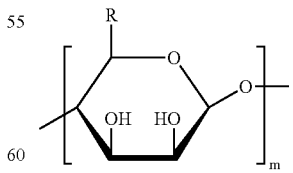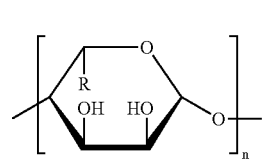

R = $CO_2H$, C = $NNHC_6F_5$
wherein m + n = 1 h. polytetrafluoroethyleneoxide-co-difluoromethyleneoxide-α-difluoroacetic acid-ω-difluoroacetyl fluorescein alginate of the formula

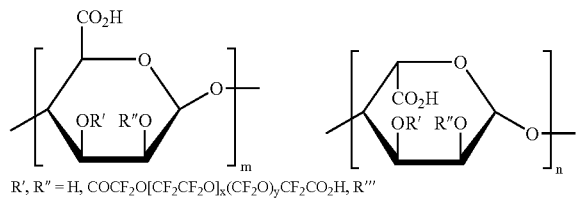

R', R'' = H, COCF$_2$O[CF$_2$CF$_2$O]$_x$(CF$_2$O)$_y$CF$_2$CO$_2$H, R'''

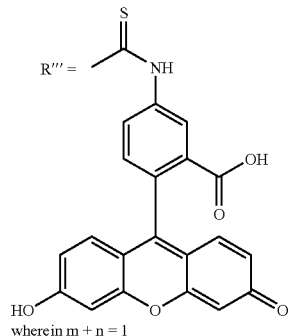

wherein m + n = 1 i. Polytetrafluoroethyleneoxide-co-difluoromethyleneoxide-α-difluoroacetic acid-ω-difluoroacetyl propylene glycol alginate of the formula

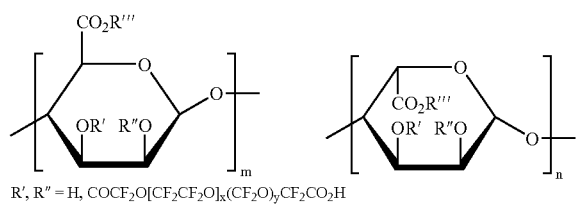

R', R'' = H, COCF$_2$O[CF$_2$CF$_2$O]$_x$(CF$_2$O)$_y$CF$_2$CO$_2$H
R''' = H, CH$_2$CH(OH)CH$_3$
wherein m + n = 1 j. perfluorobenzamide alginate of the formula

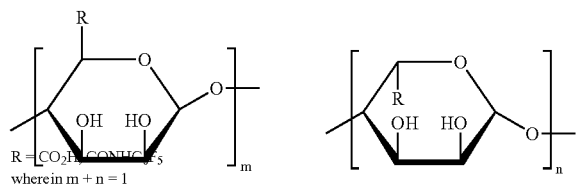

R = CO$_2$H, CONHC$_6$F$_5$
wherein m + n = 1 k. perfluoroaniline alginate of the formula

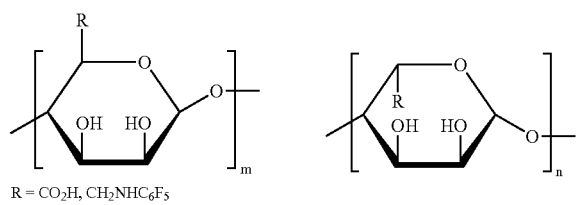

R = CO$_2$H, CH$_2$NHC$_6$F$_5$
wherein m + n = 1 l. 3-[(hexafluoropropyl)-2-hydroxy] propyleneglycol alginate of the formula

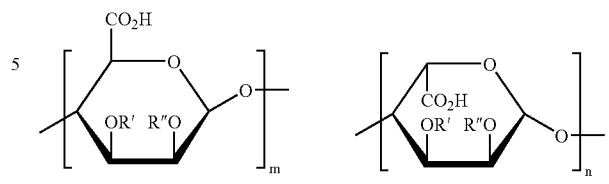

R', R'' = H, CF$_2$CF(OH)CF$_3$, CH$_2$CH(OH)CH$_2$O(CH$_2$)$_2$OCF$_2$CF(OH)CF$_3$
wherein m + n = 1 m. polytetrafluoroethyleneoxide-co-difluoromethyleneoxide-α-tolylurethane-ω-tolylisocyanate propylene glycol alginate of the formula

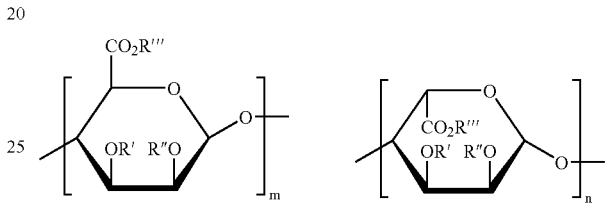

R', R'' = H, —NHCOC$_6$H$_3$[CH$_3$]NHCO$_2$[CF$_2$CF$_2$O]$_x$(CF$_2$O)$_y$CONHC$_6$H$_3$(NCO)CH$_3$;
R''' = H, CH$_2$CH(OH)CH$_3$
wherein m + n = 1 n. perfluoro-3,6,9-trioxatridecanoate alginate of the formula

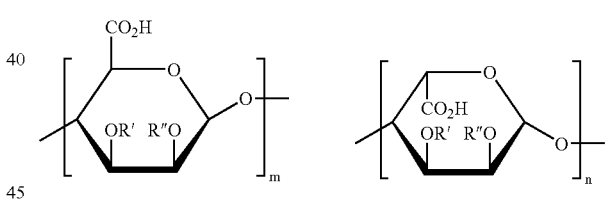

R', R'' = H, COCF$_2$O(CF$_2$)$_2$O(CF$_2$)$_2$O(CF$_2$)$_3$CF$_3$
wherein m + n = 1 o. 3,5,5''-tris(trifluoromethyl)octafluorohexanoate alginate of the formula

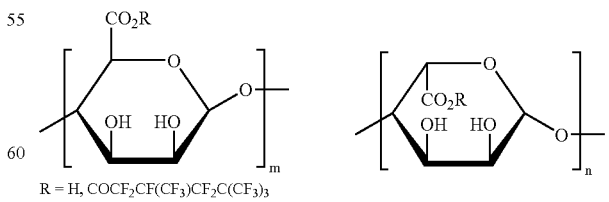

R = H, COCF$_2$CF(CF$_3$)CF$_2$C(CF$_3$)$_3$
m = 0.70–0.3  n = 0.3–0.7
wherein m + n = 1 p. 3,5,5'-tris(trifluoromethyl)octafluorohexanoate propylene glycol alginate of the formula

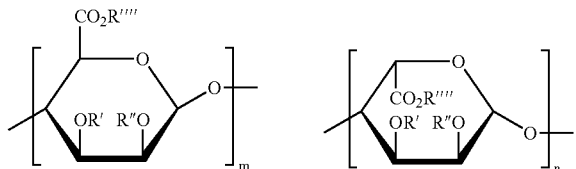

R', R" = H, COCF₂CF(CF₃)CF₂C(CF₃)₃
R''' = H, CH₂CH(OH)CH₃, CH₂CH(CH₃)OCOCF₂CF(CF₃)CF₂C(CF₃)₃
wherein m + n = 1 q. methyl perfluorohexadecanoate alginate of the formula

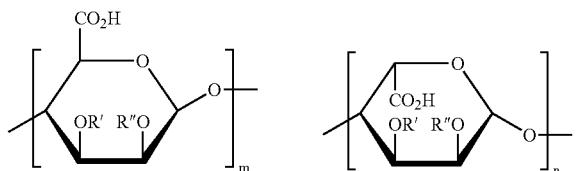

R', R" = H, COC₁₅F₃₁
wherein m + n = 1 r. heptafluorobutyryl hydroxyethyl starch, and
s. perfluorotri-n-butylamine alginate.

3. The fluorinated and/or paramagnetic polymer according to claim 1, wherein M is selected from the group consisting of gadolinium (III), iron (III), manganese (II and II), chromium (III), copper (II), dysprosium (III), terbium (III), holmium (III), erbium (III), and europium (III).

4. The fluorinated and/or paramagnetic polymer according to claim 1, wherein
   a. In Formula I $R_1$ is OH or OX, $R_2$ is OH or OX, $R_3$ is OH, and $R_4$ is C=O;
   b. In Formula II $R_1$ is OH or OX, $R_2$ is OH or OX, $R_3$ is OH, and $R_4$ is C=O;
   c. In Formula III $R_1$ is OH, $R_2$ is OH, and $R_3$ is H, N(X)₃ and
   d. In Formula IV $R_1$ is OH or —OA(X)O—, $R_2$ is OH or —OA(X)O—, and M is gadolinium (III), iron (III), manganese (II) or dysprosium (III).

5. The fluorinated and/or paramagnetic polymer according to claim 1, wherein
   X is fluoroalkyl, fluoroaryl, fluoroacyl, perfluoroalkyl, perfluoroaryl, perfluoroacyl, perfluoropolymer, fluoroamine, fluorocarbamate, fluorotriazine, fluorosulfonylalkyl derivatives, F, $CF_3$, $COC_xF_y$, $CF_3CO_2$, $C_xF_yH_z$, $([CH_2]_mO)_x(CH_2CF_2O)_y(CF_2CF_2O)_z(CF_2)_2CF_2CH_2O$ $(CH_2)_pOH$, $CH_2C(OH)C_xF_yH_z$, $C_xF_yH_zO_p$, $COC_xF_yH_z$, $OCH_2C_xF_z[C_xF_zO]_mF$, $CH_2C(CH_3)CO_2C_xH_z(CF_2)_mCF_3$, $CH_2(CF_2O)_x(CF_2CF_2O)_y(CF_2O)_zCF_2CH_2OH$, $NHC_xF_yH_zO_p$, $CH_2CF_2O[CF_2CF_2O]_mCF_2OCF_2CH_2OH$, $COC_xH_z(CF_2)_mCF_3$, $CO-CF_2O[CF_2CF_2O]_nCF_2OCF_2CO_2H$, $CO-CF(CF_3)[CF(CF_3)CF_2O]_mF$ $([CH_2]_mO)_x(CH_2CF_2O)_y(CF_2CF_2O)_zCF_2CH_2O(CH_2)_pOH$, $SO_2[CF_2]_xCF_3$, $CF_3SO_3$, $N[C_xF_yH_z]_p$, $C_xH_zCO_2C_xH_z(CF_2)_mCF_3$, or $COC_xF_y[C_pF_zO]_mF$;
   Y represents $CH_2C(OH)CH_3$;
   m, p, x, y, z represents 0–150 and
   n is from 10–10,000 inclusive.

6. A method of preforming magnetic resonance imaging (MRI) which comprises:
   a. administering an effective amount of one or more fluorinated and/or paramagnetic polymers of claim 1 to a patient;
   b. subjecting the patient to an MRI of a tissue/organ where the administered polymer is expected to accumulate; and
   c. evaluating the tissue/organ from the MRI images obtained.

7. The method according to claim 6 wherein the polymer is a fluorinated polyuronide.

8. The method according to claim 6, wherein the polymer is a paramagnetic polyuronide.

* * * * *